United States Patent [19]

Birbaum et al.

[11] Patent Number: 5,736,597
[45] Date of Patent: Apr. 7, 1998

[54] STABILIZED ORGANIC MATERIAL

[75] Inventors: Jean-Luc Birbaum, Fribourg; Jean Rody, Riehen; Mario Slongo, Tafers, all of Switzerland; Andreas Valet, Eimeldingen, Germany; Roland A. E. Winter, Armonk, N.Y.

[73] Assignee: Ciba-Geigy Corporation, Tarrytown, N.Y.

[21] Appl. No.: 143,525

[22] Filed: Oct. 26, 1993

Related U.S. Application Data

[63] Continuation of Ser. No. 978,064, Nov. 18, 1992, abandoned, which is a continuation of Ser. No. 611,207, Nov. 8, 1990, abandoned, which is a continuation-in-part of Ser. No. 446,369, Dec. 5, 1989, abandoned.

[51] Int. Cl.⁶ ......................................... C08K 5/34
[52] U.S. Cl. .......................... 524/100; 524/99; 524/102; 524/103; 252/401; 252/403
[58] Field of Search ............................ 252/401, 403; 524/99, 100, 102, 103

[56] References Cited

U.S. PATENT DOCUMENTS

| | | | |
|---|---|---|---|
| 3,244,708 | 4/1966 | Duennenberger et al. | 260/248 |
| 3,249,608 | 5/1966 | Biland et al. | 260/248 |
| 3,423,360 | 1/1969 | Huber et al. | 260/47 |
| 3,843,371 | 10/1974 | Piller et al. | 96/84 R |
| 4,619,956 | 10/1986 | Susi | 524/87 |
| 4,812,498 | 3/1989 | Nakahara et al. | 524/100 |
| 4,826,978 | 5/1989 | Migdal et al. | 544/216 |
| 5,461,151 | 10/1995 | Waterman | 544/216 |

FOREIGN PATENT DOCUMENTS

| | | |
|---|---|---|
| 0483488 | 5/1992 | European Pat. Off. |
| 484695 | 3/1970 | Switzerland |

OTHER PUBLICATIONS

WPI Acc. No.: 70-23529R/14.

*Primary Examiner*—Kriellion S. Morgan
*Attorney, Agent, or Firm*—Luther A. R. Hall

[57] ABSTRACT o-Hydroxyphenyl-s-triazines of the formula I

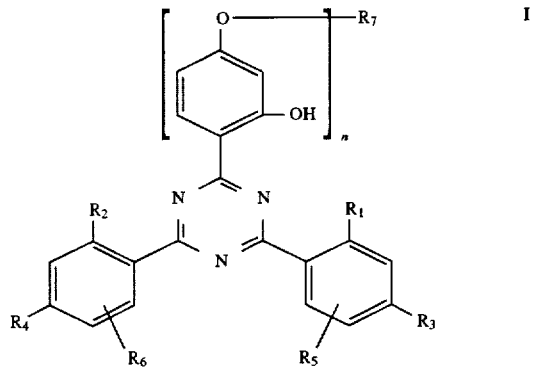

in which n is 1 to 4 and $R_1$ to $R_7$ are as defined in claim 1, can be used, in combination with sterically hindered amines of the polyalkylpiperidine type, for stabilizing organic polymers. Some of these compounds are novel and can also be used without polyalkylpiperidine.

19 Claims, No Drawings

STABILIZED ORGANIC MATERIAL

This is a continuation of Ser. No. 07/978,064, filed on Nov. 18, 1992, which is a continuation of Ser. No. 07/611,207, filed on Nov. 8, 1990, which is a continuation-in-part of application Ser. No. 446,369, filed on Dec. 5, 1989, all now abandoned.

The present invention relates to an orgarnic material containing, as stabilizers, a mixture of a sterically hindered amine and an o-hydroxyphenyl-s-triazine, and to novel o-hydroxyphenyl-s-triazine.

It is already known from U.S. Pat. No. 4,619,956 that polymers can be stabilized against the action of light, moisture and oxygen by adding a mixture of a sterically hindered amine and an o-hydroxyphenyl-s-triazine. The triazines used in this context contain at least one phenyl group carrying a hydroxyl group in the o-position.

Triazine compounds of this type are relatively sparingly soluble in many substrates and tend to migrate. In accordance with the present invention, similar triazine derivatives which have an improved compatibility with or solubility in organic polymers are used.

The invention relates to an organic material which has been stabilized against damage caused by light, heat and oxygen and which contains (a) at least one sterically hindered amine of the polyalkylpiperidine type and (b) at least one o-hydroxyphenyl-s-triazine, wherein the triazine compound (b) is a compound of the formula I

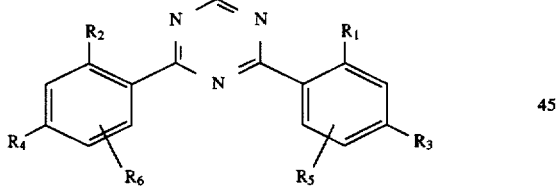

in which n is 1 to 4, $R_1$ and $R_2$ independently of one another are H, OH, $C_1$–$C_{12}$alkyl, cyclohexyl or trifluoromethyl, $R_3$ and $R_4$ independently of one another are H, OH, $C_1$–$C_{12}$alkyl, cyclohexyl, $C_1$–$C_{18}$-alkoxy or halogen and, in the event that n=1, can also be a radical —$OR_7$.

$R_5$ and $R_6$ independently of one another are H, $C_1$–$C_{12}$alkyl or halogen.

$R_7$, if n is 1, is a) $C_1$–$C_{18}$alkyl which is substituted by one or more of the groups OH, $C_1$–$C_{18}$alkoxy, $C_3$–$C_{18}$alkenoxy, halogen, phenoxy (which is unsubstituted or substituted by $C_1$–$C_{18}$alkyl, $C_1$–$C_{18}$alkoxy or halogen), furyloxy,

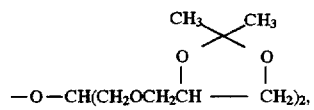

—COOH, —$COOR_8$, —$CONH_2$, —$CONHR_9$, —$CON(R_9)(R_{10})$, —$NH_2$, —$NHR_9$, —$N(R_9)(R_{10})$, —$NHCOR_{11}$, —CN and/or by —O—CO—$R_{11}$.

b) $C_4$–$C_{50}$alkyl which is interrupted by one or more O and can be substituted by OH or/and glycidyloxy, c) $C_3$–$C_6$alkenyl, d) glycidyl or a group

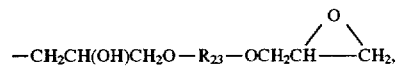

e) cyclohexyl which is unsubstituted or substituted by OH or —$OCOR_{11}$.

f) $C_7$–$C_{11}$phenylalkyl which is unsubstituted or substituted by OH, Cl or $CH_3$.

g) —CO—$R_{12}$ or h) —$SO_2$—$R_{13}$.

and if n is 2, $R_7$ is a) $C_2$–$C_{16}$alkylene, b) $C_4$–$C_{12}$alkenylene, c) xylylene, d) $C_3$–$C_{20}$alkylene which is interrupted by one or more O and/or substituted by OH.

e) a group —$CH_2CH(OH)CH_2O$—$R_{15}$—$OCH_2CH(OH)CH_2$—, —CO—$R_{16}$—CO—, —CO—NH—$R_{17}$—NH—CO— or —$(CH_2)_m$—COO—$R_{18}$—OOC—$(CH_2)_m$— (in which m is 1 to 3) or

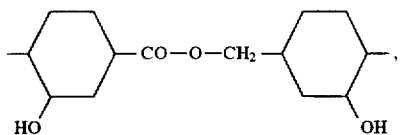

and if n is 3, $R_7$ is a group

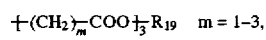

and if n is 4, $R_7$ is a group

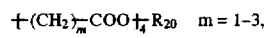

$R_8$ is $C_1$–$C_{18}$alkyl, $C_3$–$C_{18}$alkenyl, $C_3$–$C_{20}$alkyl which is interrupted by one or more O, N or S and/or substituted by OH, $C_1$–$C_4$alkyl which is substituted by —$P(O)(OR_{14})_2$, —$N(R_9)(R_{10})$ or —$OCOR_{11}$ and/or OH, $C_3$–$C_{18}$alkenyl, glycidyl or $C_7$–$C_{11}$phenylalkyl.

$R_9$ and $R_{10}$ independently of one another are $C_1$–$C_{12}$alkyl, $C_3$–$C_{12}$alkoxyalkyl, $C_4$–$C_{16}$dialkylaminoalkyl or $C_5$–$C_{12}$cycloalkyl, or $R_9$ and $R_{10}$ together are $C_3$–$C_9$alkylene or $C_3$–$C_9$oxaalkylene or $C_3$–$C_9$azaalkylene.

$R_{11}$ is $C_1$–$C_{18}$alkyl, $C_2$–$C_{18}$alkenyl or phenyl, $R_{12}$ is $C_1$–$C_{18}$alkyl, $C_2$–$C_{18}$alkenyl, phenyl, $C_1$–$C_{12}$alkoxy, phenoxy, $C_1$–$C_{12}$alkylamino or $C_6$–$C_{12}$arylamino or a group —$R_{24}$—COOH or —NH—$R_{17}$—NCO.

$R_{13}$ is $C_1$–$C_{12}$alkyl, $C_6$–$C_{12}$aryl or $C_7$–$C_{14}$alkaryl, $R_{14}$ is $C_1$–$C_{12}$alkyl or phenyl, $R_{15}$ is $C_2$–$C_{10}$alkylene, $C_4$–$C_{50}$alkylene which is interrupted by one or more O, phenylene or a group -phenylene-X-phenylene- in which X is —O—, —S—, —$SO_2$—, —$CH_2$— or —$C(CH_3)_2$—, $R_{16}$ is $C_2$–$C_{10}$alkylene, $C_1$–$C_{10}$oxaalkylene or $C_2$–$C_{10}$thiaalkylene, $C_6$–$C_{12}$arylene or $C_2$–$C_6$alkenylene, $R_{17}$ is $C_2$–$C_{10}$alkylene, phenylene, tolylene, diphenylenemethane or a group

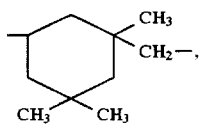

$R_{18}$ is $C_2$–$C_{10}$alkylene or $C_4$–$C_{20}$alkyene which is interrupted by one or more O, $R_{19}$ is $C_3$–$C_{12}$alkanetriyl, $R_{20}$ is $C_4$–$C_{12}$alkanetetryl, $R_{23}$ is $C_2$–$C_{10}$alkylene, phenylene or a group

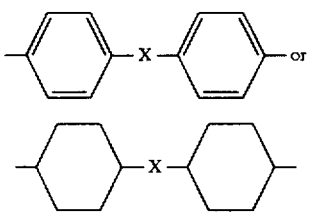

wherein X is O, S, $SO_2$, $CH_2$ or $C(CH_3)_2$, and $R_{24}$ is $C_2$–$C_{14}$alkylene, vinylene or o-phenylene.

If one of the substitutents in formula I is $C_1$–$C_{12}$alkyl, it can be unbranched or branched alkyl, for example methyl, ethyl, propyl, isopropyl, n-butyl, i-butyl, s-butyl or t-butyl, pentyl, hexyl, heptyl, octyl, 2-ethylhexyl, di-t-octyl, nonyl, decyl, undecyl or dodecyl. As $C_1$–$C_{18}$alkyl, $R_8$, $R_{11}$ and $R_{12}$ can additionally be, for example, tetradecyl, hexadecyl or octadecyl.

As $C_1$–$C_{18}$alkoxy, $R_3$ and $R_4$ are preferably $C_1$–$C_{12}$alkoxy. The alkoxy radical is preferably unbranched. Examples of these are methoxy, ethoxy, propoxy, butoxy, hexyloxy, octyloxy, decyloxy or dodecyloxy.

As substituted $C_1$–$C_{12}$alkyl, $R_7$ can be substituted by one or more of the groups OH, $C_1$–$C_{18}$alkoxy, halogen, phenoxy which is unsubstituted or substituted by $C_1$–$C_{18}$alkyl, $C_1$–$C_{18}$alkoxy or halogen, —COOH, —COO$R_8$, —CONH$_2$, —CONH$R_9$, —CON($R_9$)($R_{10}$), —NH$_2$, —NH$R_9$, —NH($R_9$)($R_{10}$), —NHCO$R_{11}$, —CN or —OCO$R_{11}$. The following groups are examples of such substituted alkyl groups: —CH$_2$CH$_2$OH, —CH$_2$CH(OH)CH$_3$, —CH$_2$CH(OH)C$_2$H$_5$, —CH$_2$CH(OH)C$_6$H$_{13}$, —CH$_2$CH(OH)C$_{10}$H$_{21}$, —CH$_2$CH$_2$OCH$_3$, —CH$_2$CH$_2$OC$_2$H$_5$, —CH$_2$CH$_2$OC$_4$H$_9$, —(CH$_2$)$_3$OH, —CH$_2$CH(OH)CH$_2$OC$_4$H$_9$, —CH$_2$CH(OH)CH$_2$OC$_{12}$H$_{25}$, —CH$_2$CH$_2$Ophenyl, —CH$_2$CH$_2$Cl, —CH$_2$CH(OH)CH$_2$Ophenyl,

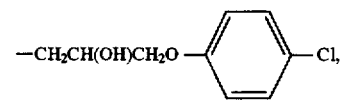

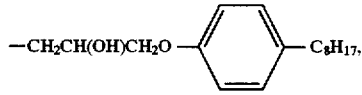

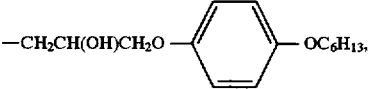

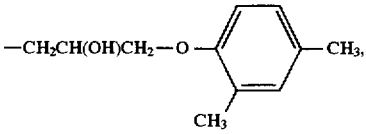

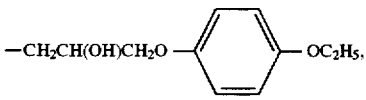

—CH$_2$COOH, —CH$_2$CH$_2$COOH, —CH$_2$COOC$_2$H$_5$, —CH$_2$COOC$_8$H$_{17}$, —CH$_2$CH$_2$COOCH$_3$, —CH$_2$CH$_2$COOC$_4$H$_9$, —CH$_2$CH$_2$COOC$_{12}$H$_{25}$, —CH$_2$CONH$_2$, —CH$_2$CONHC$_4$H$_9$, —CH$_2$CON(C$_4$H$_9$)$_2$, —CH$_2$CH$_2$CONHC$_{12}$H$_{25}$, —CH$_2$CH$_2$CON(C$_2$H$_5$)$_2$, —CH$_2$CH$_2$NH$_2$, —CH$_2$CH$_2$N(CH$_3$)$_2$, —(CH$_2$)$_3$—NH$_2$, —(CH$_2$)$_3$—NHC$_4$H$_9$, —(CH$_2$)$_3$N(CH$_3$)$_2$, —(CH$_2$)$_3$N(C$_2$H$_5$)$_2$, —(CH$_2$)$_3$NHCOCH$_3$, —(CH$_2$)$_3$NHCOC$_7$H$_{15}$, —CH$_2$CH$_2$CN, —CH$_2$CH$_2$OCOC$_3$H$_7$, —CH$_2$CH$_2$OCOC$_{17}$H$_{35}$, —CH$_2$CH(CH$_3$)—OCOCH$_3$, —CH$_2$CH(OCOCH$_3$)CH$_2$OC$_8$H$_{17}$ or —CH$_2$CH(OCOC$_7$H$_{15}$)CH$_2$Ophenyl.

As $C_3$–$C_6$alkenyl, $R_7$ can, for example, be allyl, methallyl or 2-butenyl. As $C_3$–$C_{18}$alkenyl, $R_8$ can additionally also be, for example, octenyl, dodecenyl or oleyl. As $C_2$–$C_{18}$alkenyl, $R_{11}$ and $R_{12}$ can additionally also be vinyl.

As $C_7$–$C_{11}$phenylalkyl which is unsubstituted or substituted by OH, Cl or CH$_3$, $R_7$ and $R_8$ can, for example, be phenylethyl, 2-hydroxy-2-phenylethyl, 2-phenylpropyl, 3-phenylpropyl, 4-chlorobenzyl or 4-methylbenzyl, but especially benzyl.

As $C_2$–$C_{16}$alkylene, $R_7$ can be unbranched or branched alkylene, for example di-, tri-, tetra-, hexa-, octa-, deca- or dodeca-methylene, 2,2-dimethyl-prop-1,3-ylene or 1,2-propylene. As $C_4$–$C_{12}$alkenylene, $R_7$ can, in particular, be 2-buten-1,4-ylene. As $C_3$–$C_{20}$alkylene which is interrupted by O and/or substituted by OH, $R_7$ can, for example, be one of the groups —CH$_2$CH(OH)CH$_2$—, —CH$_2$CH$_2$OCH$_2$CH$_2$— or —CH$_2$CH(OH)CH$_2$O—(CH$_2$)$_x$—OCH$_2$CH(OH)CH$_2$— in which x=2–10.

As $C_3$–$C_{20}$alkyl which is interrupted and/or substituted by OH, $R_8$ can, in particular, be alkyl which is substituted by OH or alkyl which is interrupted by O and substituted by OH. Examples of these are the groups —CH$_2$CH$_2$OH, —CH$_2$CH(OH)CH$_3$, —CH$_2$CH(OH)C$_6$H$_{13}$, —CH$_2$CH$_2$OC$_4$H$_9$, —CH$_2$CH$_2$OCH$_2$CH$_2$OH or —CH$_2$CH$_2$(OCH$_2$CH$_2$)$_p$OH in which p=2–9.

As $C_1$–$C_4$alkyl which is substituted by —P(O)(OR$_{14}$)$_2$, —N(R$_9$)(R$_{10}$) or —OCOR$_{11}$, R$_8$ can, for example, be —CH$_2$CH$_2$P(O)(OC$_2$H$_5$)$_2$, —CH$_2$P(O)(OC$_6$H$_{13}$)$_2$, —CH$_2$CH$_2$N(CH$_3$)$_2$, —CH$_2$CH$_2$CH$_2$N(C$_2$H$_5$)$_2$, —CH$_2$CH$_2$OCOC$_7$H$_{15}$ or —CH$_2$CH$_2$OCOCH=CH$_2$.

As $C_3$–$C_{12}$alkoxyalkyl, $R_9$ and $R_{10}$ can, in particular, be 2-($C_1$–$C_{10}$alkoxy)-ethyl, for example 2-methoxyethyl, 2-butoxyethyl or 2-octyloxyethyl. As $C_4$–$C_{16}$dialkylaminoalkyl, $R_9$ and $R_{10}$ can, for example, be 2-dibutylaminoethyl, 2-diethylaminoethyl or 3-dimethylaminopropyl.

As $C_5$–$C_{12}$cycloalkyl, $R_9$ and $R_{10}$ can, for example, be cyclopentyl, cyclooctyl or cyclododecyl, but especially cyclohexyl. If $R_9$ and $R_{10}$ together are $C_3$–$C_9$alkylene, $C_3$–$C_9$oxaalkylene or $C_3$–$C_9$azaalkylene, they form, together with the N atom to which they are attached, a heterocyclic ring, for example a pyrrolidine, piperidine, 2,6-dimethylpiperidine, morpholine, dimethylmorpholine or piperazine ring.

As $C_1$–$C_{12}$alkoxy, $R_{12}$ can, for example, be methoxy, ethoxy, butoxy, hexyloxy, octyloxy, decyloxy or dodecyloxy.

As $C_1$–$C_{12}$alkylamino or $C_6$–$C_{12}$arylamino, $R_{12}$ can, for example, be hexylamino, dodecylamino, phenylamino, naphthylamino or biphenylylamino.

As $C_2$–$C_{10}$alkylene, $R_{16}$, $R_{17}$ and $R_{18}$ can be unbranched or branched alkylene, for example 1,2-ethylene, tri-, tetra-, penta-, hexa-, octa- or deca-methylene, 1,2-propylene or 2,2-dimethyltrimethylene, while as oxaalkylene or thiaalkylene, $R_{16}$ can, for example, be 2-oxatrimethylene, 3-oxapentamethylene, 3-thiapentamethylene or 2-thiatrimethylene. As $C_2$–$C_6$alkenylene, $R_{16}$ can, in particular, be —CH=CH—.

As $C_6$–$C_{12}$arylene, $R_{16}$ and $R_{17}$ can, for example, be phenylene, naphthylene or biphenylene. As $C_7$–$C_{15}$alkylarylene, $R_{17}$ can, in particular, be tolylene.

As $C_4$–$C_{20}$alkylene which is interrupted by O, $R_{18}$ can be interrupted by 1–9 O atoms and can, in particular, be the divalent radical formed by removing the two hydroxyl groups from a polyethylene glycol or polypropylene glycol.

In the substituents, aryl on its own or in combined radicals is preferably phenyl, naphthyl or biphenylyl.

Compounds of the formula I which are preferred as the component (b) are those in which n is 1 to 4, $R_1$ and $R_2$ independently of one another are H, OH or $C_1$–$C_4$alkyl, $R_3$ and $R_4$ independently of one another are H, OH, $C_1$–$C_4$alkyl, $C_1$–$C_4$alkoxy, halogen or a radical —$OR_7$, $R_5$ and $R_6$ independently of one another are H or $C_1$–$C_4$alkyl, $R_7$, if n is 1, is a) $C_1$–$C_{18}$alkyl which is substituted by one or more of the groups OH, $C_1$–$C_{18}$alkoxy, allyloxy, phenoxy, furyloxy,

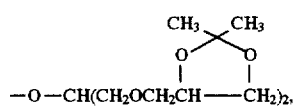

—$COOR_8$, —$CON(R_9)(R_{10})$ and/or by —$OCOR_{11}$, b) $C_4$–$C_{50}$alkyl which is interrupted by one or more O and can be substituted by OH or/and glycidyloxy, c) allyl, glycidyl or benzyl, d) cyclohexyl or hydroxycyclohexyl, and if n is 2, $R_7$ is $C_4$–$C_{12}$alkylene, $C_4$–$C_6$alkenylene, xylylene, $C_3$–$C_{20}$alkylene which is interrupted by one or more O and/or substituted by OH, or $R_7$ is a group —$CH_2CH(OH)CH_2O$—$R_{15}$—$OCH_2CH(OH)CH_2$—, —CO—$R_{16}$—CO—, —$CH_2$—COO—$R_{18}$—OOC—$CH_2$— or

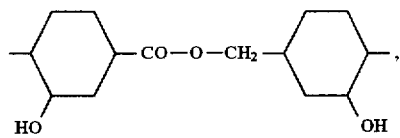

and if n is 3, $R_7$ is a group

and if n is 4,
$R_7$ is a group

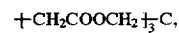

$R_8$ is $C_1$–$C_{12}$alkyl, $C_3$–$C_{18}$alkenyl, $C_3$–$C_{20}$alkyl which is interrupted by one or more O and/or substituted by OH or $R_8$ is $C_1$–$C_4$alkyl which is substituted by —$P(O)(OR_{14})_2$.

$R_9$ and $R_{10}$ are $C_1$–$C_6$alkyl or $R_9$ and $R_{10}$ together are pentamethylene or 3-oxapentamethylene.

$R_{11}$ is $C_1$–$C_{12}$alkyl, $C_2$–$C_5$alkenyl or phenyl, $R_{14}$ is $C_1$–$C_4$alkyl.

$R_{15}$ is $C_2$–$C_8$alkylene, $C_4$–$C_{50}$alkylene which is interrupted by one or more O, or is a group

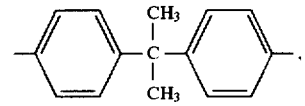

$R_{16}$ is $C_2$–$C_8$alkylene, $C_2$–$C_6$oxaalkylene or $C_2$–$C_6$thiaalkylene and $R_{18}$ is $C_4$–$C_8$alkylene or $C_4$–$C_{12}$alkylene which is interrupted by one or more O.

$R_1$ and $R_2$ are preferably hydrogen, chlorine or $C_1$–$C_4$alkyl, particularly hydrogen or methyl. $R_3$ and $R_4$ are preferably hydrogen, chlorine or $C_1$–$C_4$alkyl, particularly hydrogen, chlorine or methyl. $R_5$ and $R_6$ are preferably hydrogen.

Compounds of the formula I which are particularly preferred as component (b) are those in which n is 1, 2 or 4, $R_1$ and $R_2$ independently of one another are H or $CH_3$, $R_3$ and $R_4$ independently of one another are H, $CH_3$ or Cl, $R_5$ and $R_6$ are hydrogen, $R_7$, if n is 1, is a) $C_1$–$C_{14}$alkyl which is substituted by one or more of the groups OH, $C_1$–$C_{15}$alkoxy, allyloxy, phenoxy, furyloxy,

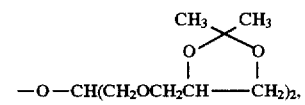

—$COOR_8$, —$CON(R_9)(R_{10})$ and/or by —$OCOR_{11}$, b) $C_6$–$C_{45}$alkyl which is interrupted by one or more O and can be substituted by OH or/and glycidyloxy, c) glycidyl or d) hydroxycyclohexyl, and if n is 2, $R_7$ is $C_6$–$C_{12}$alkylene, 2-butenylene-1,4, xylylene, $C_3$–$C_{20}$alkylene which is interrupted by one or more O or substituted by OH, or $R_7$ is a group —$CH_2CH(OH)CH_2O$—$R_{15}$—$OCH_2CH(OH)CH_2$—, —CO—R$_{16}$—CO—, —CH$_2$—COO—R$_{18}$—OOC—CH$_2$— or

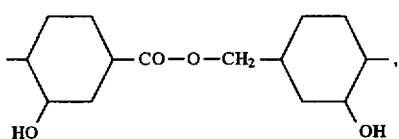

and if n is 4,
R$_7$ is

R$_8$ is C$_4$–C$_{10}$alkyl, oleyl, C$_3$–C$_{20}$alkyl which is interrupted by one or more O and/or substituted by OH, or R$_8$ is —CH$_2$P(O)(OR$_{14}$)$_2$,
R$_9$ and R$_{10}$ are C$_2$–C$_6$alkyl
R$_{11}$ is C$_6$–C$_{10}$alkyl, C$_2$–C$_3$alkenyl R$_{14}$ is C$_1$–C$_4$alkyl,
R$_{15}$ is C$_2$–C$_8$alkylene, C$_{10}$–C$_{45}$alkylene which is interrupted by more than one O, or is a group

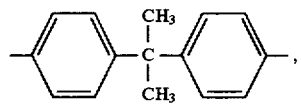

R$_{16}$ is C$_4$–C$_8$alkylene and R$_{18}$ is C$_4$–C$_8$alkylene.

A further preferred group of compounds of the formula I is formed by those in which n is 1 or 2 and, if n is 1, R$_7$ is a group —CH$_2$CH(OH)CH$_2$—OR$_{21}$ in which R$_{21}$ is C$_1$–C$_{18}$alkyl, allyl, phenyl, furyl, C$_6$–C$_{12}$-alkanoyl or C$_3$–C$_5$alkenoyl and, if n is 2, R$_7$ is a group —CH$_2$CH(OH)CH$_2$O—R$_{15}$—OCH$_2$CH(OH)CH$_2$— in which R$_{15}$ is as defined above.

The following compounds are examples of individual compounds of the formula I

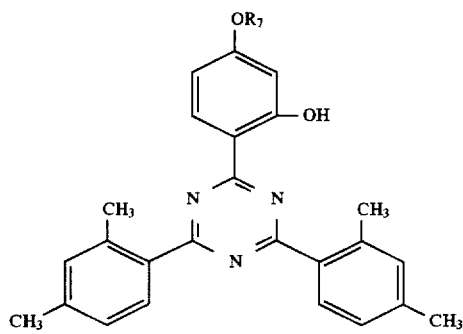

R$_7$ = CH$_2$ phenyl
—CH$_2$CH$_2$OH
—CH$_2$CH$_2$OCOCH$_3$
—CH$_2$CH$_2$OCOCH=CH$_2$
—CH$_2$CH(OH)CH$_2$OC$_8$H$_{17}$
—CH$_2$CH(OH)CH$_2$O(CH$_2$)$_{12-14}$CH$_3$
—CH$_2$CH(OH)CH$_2$O phenyl
—CH$_2$CH(OH)CH$_2$OCOC(CH$_3$)=CH$_2$

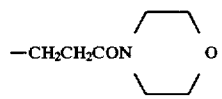

—CH$_2$COOH
—CH$_2$CH$_2$COOC$_4$H$_9$
—CH$_2$COOC$_8$H$_{17}$
—CH$_2$COO(CH$_2$CH$_2$O)$_7$H
—CH$_2$COOCH$_2$CH(OH)CH$_2$OCOCH=CH$_2$
—CH$_2$COOCH$_2$CH(CH$_3$)OCH$_2$CH(CH$_3$)OCH(CH$_3$)CH$_3$
—CH$_2$COOCH$_2$P(O)(OC$_2$H$_5$)$_2$
—CH$_2$COOCH$_2$CH(OH)CH$_2$P(O)(OC$_4$H$_9$)$_2$
—CH$_2$COO(CH$_2$)$_7$CH=CHC$_8$H$_{17}$
—CH$_2$COOCH$_2$CH$_2$OCH$_2$CH$_2$OC$_6$H$_{13}$
—CH$_2$CON(C$_2$H$_5$)$_2$

—CH$_2$CH$_2$CON⟨  ⟩O

—CH$_2$CONHCH$_2$CH$_2$CH$_2$N(CH$_3$)$_2$
—CH$_2$CONHC$_8$H$_{17}$
—CH$_2$CON(C$_8$H$_{17}$)$_2$

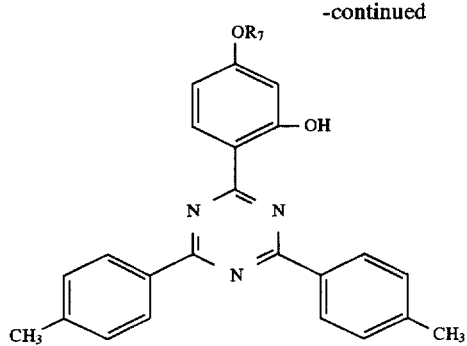

R₇ = —CH₂COOC₂H₅
—CH₂COOCH₂CH₂OCH₃
—CH₂COOCH₂CH=CH-phenyl
—CH₂CH(OH)CH₂O(CH₂)₁₂₋₁₄CH₃

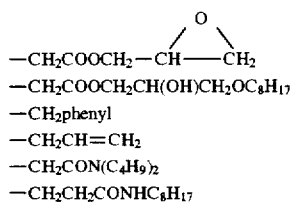
—CH₂COOCH₂CH(OH)CH₂OC₈H₁₇
—CH₂phenyl
—CH₂CH=CH₂
—CH₂CON(C₄H₉)₂
—CH₂CH₂CONHC₈H₁₇

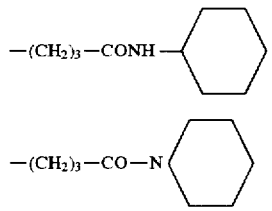

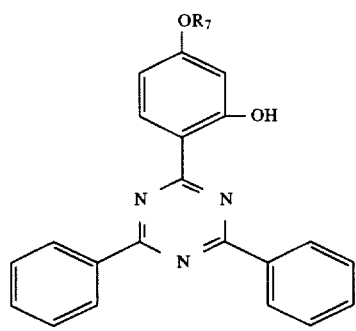

—CO—OC₆H₁₃
—CH₂CH₂Cl
—CH₂CH₂CN

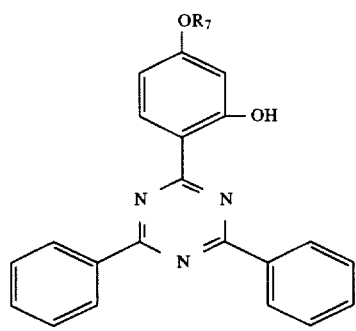

R₇ = —CH₂CH(OH)phenyl
—CH₂CH(OH)CH₂O(CH₂)₁₂₋₁₄CH₃
—CH₂CH(OH)CH₂OCOphenyl
—CH₂CH(CH₃)OCOCH₃
—SO₂—C₁₂H₁₅

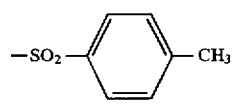

—CH₂COOC₁₀H₂₁
—CH₂CONHCH₂CH₂OCH₃
—CH₂CH₂CONHCH₂phenyl
—(CH₂)₃CONH(CH₂)₃N(C₂H₅)₂
—CH₂CONHC₁₂H₂₅

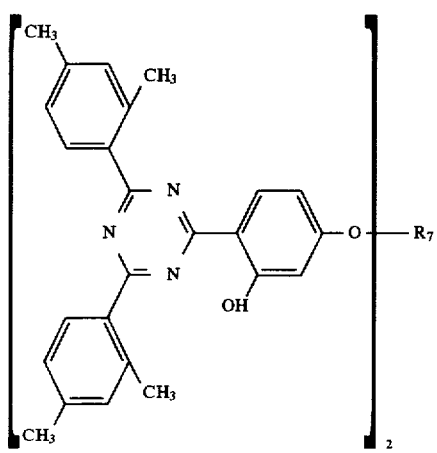
$R_7 = -CH_2CH(OH)CH_2-$
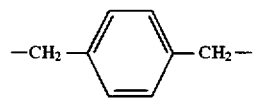
$-CH_2-CH=CH-CH_2-$
$-(CH_2)_4-$
$-(CH_2)_6-$
$-(CH_2)_8-$
$-(CH_2)_{12}-$
$-CH_2CH(OH)CH_2O-CH_2CH_2-OCH_2CH(OH)CH_2-$
$-CH_2CH(OH)CH_2O-(CH_2)_6-OCH_2CH(OH)CH_2-$
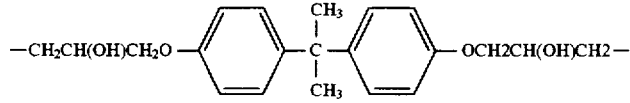
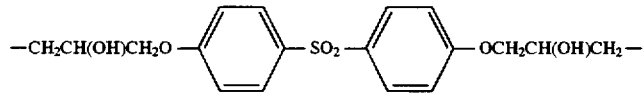
$-CH_2COO-(CH_2)_6-OCOCH_2-$
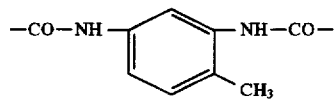
$-CO-(CH_2)_8-CO-$
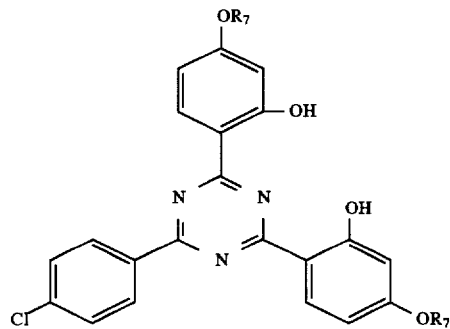

R₇= —CH₂CH(OH)CH₃
—CH₂CH₂OC₄H₉
—CH₂CH₂COC₂H₅
—CH₂COOC₈H₁₇
—CH₂CH(OH)CH₂OC₄H₉
—CH₂CH(OH)CH₂Ophenyl

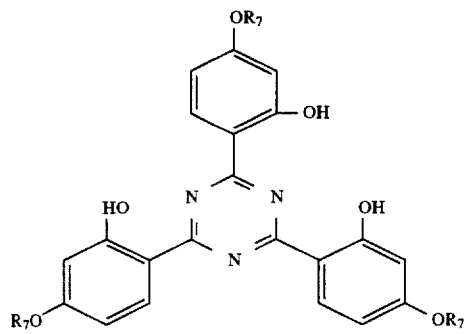

R₇= —CH₂CH₂OH
—CH₂CH₂Ophenyl
—CH₂COOC₆H₁₃
—CH₂CH₂COO(CH₂CH₂O)₃H
—CH₂CH(OH)CH₂OC₆H₁₃
—CH₂CH(OH)CH₂phenyl Some of the triazine derivatives of the formula I are known compounds. Many such compounds and also their preparation and their use as UV absorbers for organic materials are described in U.S. Pat. Nos. 3,244,708, 3,249,608 and 3,423,360. Their use in photographic materials is described in U.S. Pat. No. 3,843,371.

Another fraction of the triazine derivatives constitutes novel compounds. Compounds which are novel and are also a subject of the present invention are those of the formula Ia

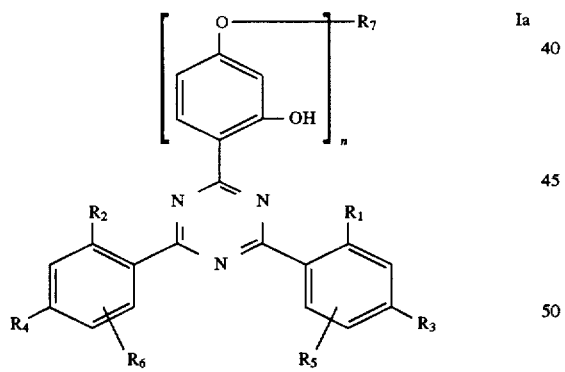

in which n
is 1 to 4,
R₁ and R₂ independently of one another are H, OH, $C_1-C_{12}$alkyl, cyclohexyl or trifluoromethyl,
R₃ and R₄ independently of one another are H, OH, $C_1-C_{12}$alkyl, cyclohexyl, $C_1-C_{18}$-alkoxy or halogen and in the event that n=1, can also be a radical —OR₇,
R₅ and R₆ independently of one another are H, $C_1-CH_{12}$alkyl or halogen,
R₇, if n is 1, is
  a) $C_1-C_{12}$alkyl which is substituted by phenoxy (which is unsubstituted or substituted by $C_1-C_{18}$alkyl, $C_1-C_{18}$alkoxy or halogen) or by a group —COOR₈, —CONH₂, —CONHR₉, —CON(R₉)(R₁₀), —NH₂, NHR₉, —N(R₉)(R₁₀) or —O—CO—R₂₂, b) $C_4-C_{50}$alkyl which is interrupted by more than one O and can be substituted by OH or/and glycidyloxy. be substituted by OH or/and glycidyloxy.
c) glycidyl or a group

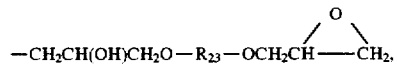

d) cyclohexyl substituted by OH or —OCOR₁₁
e) a group —CH₂CH(OH)CH₂OR₂₁
f) a group —SO₂—R₁₃,
g) a group —CO—R₁₂, and if n is 2, R₇ is
a) $C_2-C_{12}$alkylene,
b) $C_4-C_{12}$alkenylene,
c) xylylene,
d) $C_3-C_{20}$alkylene which is interrupted by one or more O and/or substituted by OH.
e) a group —CH₂CH(OH)CH₂O—R₁₅—OCH₂CH(OH)CH₂—, —(CH₂)ₘ—COO—R₁₈—OOC—(CH₂)ₘ—(wherein m is 1–3) or

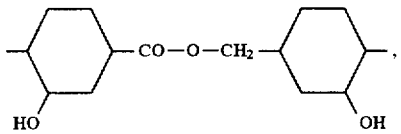

and if n is 3, R₇ is a group

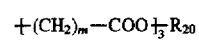

(wherein m is 1–3),
and if n is 4, $R_7$ is a group

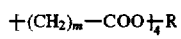

(wherein m is 1–3), $R_8$ is $C_3$–$C_{20}$alkyl which is interrupted by one or more O, N or S and can be substituted by OH, or $R_8$ is $C_1$–$C_4$alkyl which is substituted by —P(O)(OR$_{14}$)$_2$, —N(R$_9$)(R$_{10}$), or —OCOR$_{11}$ and/or OH, or $R_8$ is $C_3$–$C_{18}$alkenyl, glycidyl or $C_7$–$C_{11}$phenylalkyl, $R_9$ and $R_{10}$ independently are $C_1$–$C_{12}$alkyl, $C_3$–$C_{12}$alkoxyalkyl, $C_4$–$C_{16}$dialkylaminoalkyl or $C_5$–$C_{12}$cycloalkyl, or $R_9$ and $R_{10}$ together are $C_3$–$C_9$alkylene or $C_3$–$C_9$-oxaalkylene or $C_3$–$C_9$azaalkylene, $R_{11}$ is $C_1$–$C_{18}$alkyl, $C_2$–$C_{18}$alkenyl or phenyl, $R_{12}$ is a group —$R_{24}$—COOH or —NH—$R_{17}$—NCO, $R_{13}$ is $C_1$–$C_{12}$ alkyl, $C_6$–$C_{12}$aryl or $C_7$–$C_{14}$alkaryl $R_{14}$ is $C_1$–$C_{12}$alkyl or phenyl $R_{15}$ is $C_2$–$C_{10}$alkylene, $C_4$–$C_{50}$alkylene which is interrupted by one or more O, or $R_{15}$ is phenylene or a group -phenylene-X-phenylene- in which X is —O—, —S—, —SO$_2$—, —CH$_2$— or —C(CH$_3$)$_2$—, $R_{17}$ is $C_2$–$C_{10}$alkylene, phenylene, tolylene, diphenylenemethane or a group

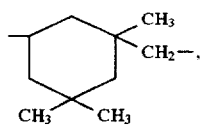

$R_{18}$ is $C_2$–$C_{10}$alkylene or $C_4$–$C_{20}$alkylene which is interrupted by one or more O, $R_{19}$ is $C_3$–$C_{12}$alkanetriyl, $R_{20}$ is $C_4$–$C_{12}$alkanetetryl, $R_{21}$ is H, $C_1$–$C_{18}$alkyl, $C_3$–$C_{18}$alkenyl, phenyl, phenyl substituted by $C_1$–$C_{12}$alkyl, $C_1$–$C_{12}$alkoxy or halogen, or $R_{21}$ is $C_2$–$C_{19}$alkanoyl, benzoyl, $C_3$–$C_{18}$alkenoyl, furyl or a group

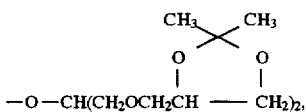

$R_{22}$ is $C_2$–$C_5$alkenyl, $R_{23}$ is $C_2$–$C_{10}$alkylene, phenylene or a group

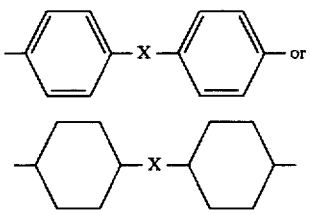

wherein X is O, S, SO$_2$, CH$_2$ or C(CH$_3$)$_2$, and $R_{24}$ is $C_2$–$C_{14}$alkylene, vinylene or o-phenylene.

Amongst these compounds of the formula Ia, preferred compounds are those in which n is 1 to 4, $R_1$ and $R_2$ independently of one another are H, OH or $C_1$–$C_4$alkyl, $R_3$ and $R_4$ independently of one another are H, OH, $C_1$–$C_4$alkyl, $C_1$–$C_4$alkoxy, halogen or a radical —OR$_7$, $R_5$ and $R_6$ independently of one another are H or $C_1$–$C_4$alkyl.

$R_7$, if n is 1, is $C_1$–$C_6$alkyl which is substituted by —COOR$_8$, —COONHR$_9$, —CON(R$_9$)(R$_{10}$) or —OCOR$_{22}$, or $R_7$ is glycidyl, hydroxycyclohexyl or a group —CH$_2$CH(OH)CH$_2$OR$_{21}$, and if n is 2, $R_7$ is $C_4$–$C_{12}$alkylene, $C_4$–$C_6$alkenylene, xylylene, $C_3$–$C_{20}$alkylene which is interrupted by one or more O and/or substituted by OH, or $R_7$ is a group —CH$_2$CH(OH)CH$_2$O—$R_{15}$—OCH$_2$CH(OH)CH$_2$—, —CH$_2$—COO—$R_{18}$—OOCCH$_2$— or

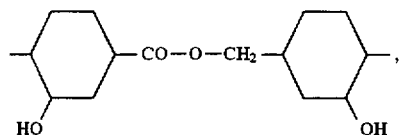

and if n is 3, $R_7$ is a group

and if n is 4, $R_7$ is a group

$R_8$ is $C_3$–$C_{20}$alkyl which is interrupted by one or more O and can be substituted by OH or $R_8$ is $C_1$–$C_4$alkyl which is substituted by —P(O)(OR$_{14}$)$_2$ or $R_8$ is $C_3$–$C_{18}$alkenyl, $R_9$ and $R_{10}$ independently are $C_1$–$C_8$alkyl or cyclohexyl or $R_9$ and $R_{10}$ together are pentamethylene or 3-oxapentamethylene, $R_{14}$ is $C_1$–$C_{14}$alkyl, $R_{15}$ is $C_2$–$C_8$alkylene, $C_4$–$C_{50}$alkylene which is interrupted by one or more O, or $R_{15}$ is a group -phenylene-X-phenylene- in which X is —O—, —CH$_2$— or —C(CH$_3$)$_2$—, $R_{18}$ is $C_4$–$C_8$alkylene or $C_4$–$C_{12}$alkylene which is interrupted by one or more O, $R_{21}$ is H, $C_4$–$C_{18}$alkyl, allyl, phenyl, furyl, $C_5$–$C_{19}$alkanoyl or $C_3$–$C_5$alkenoyl and $R_{22}$ is $C_2$–$C_5$alkenyl, in particular those in which n is 1, 2 or 4, $R_1$ and $R_2$ independently of one another are H or CH$_3$, $R_3$ and $R_4$ independently of one another are H, CH$_3$ or Cl, $R_5$ and $R_6$ are hydrogen, $R_7$, if n is 1, is $C_1C_4$alkyl which is substituted by —COOR$_8$, —CON(R$_9$)(R$_{10}$) or —O—COR$_{22}$, or $R_7$ is glycidyl, 2-hydroxycyclohexyl or a group —CH$_2$CH(OH)CH$_2$OR$_{21}$, and if n is 2, $R_7$ is $C_6$–$C_{12}$alkenylene, 2-butene-1,4-ylene, xylylene or $C_3$–$C_{20}$alkylene which is interrupted by one or more O and/or substituted by OH, or $R_7$ is a group —CH$_2$CH(OH)CH$_2$O—$R_{15}$—OCH$_2$CH(OH)CH$_2$—, —CH$_2$—COO—$R_{18}$—OOCCH$_2$— or

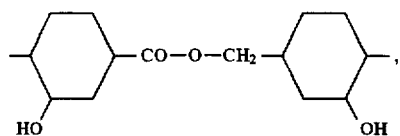

and if n is 4, $R_7$ is a group

$R_8$ is $C_3$–$C_{20}$alkyl which is interrupted by one or more O and can be substituted by OH or $R_8$ is —CH$_2$P(O)(OR$_4$)$_2$ or oleyl $R_9$ and $R_{10}$ are $C_2$–$C_6$alkyl $R_{15}$ is $C_2$–$C_8$alkylene, $C_{10}C_{45}$alkylene which is interrupted by one or more O or is a group

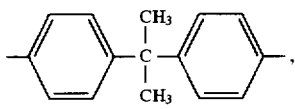

$R_{18}$ is $C_4$–$C_8$alkylene.

$R_{21}$ is H, $C_4$–$C_{15}$alkyl, allyl, phenyl, furyl, $C_5$–$C_{12}$alkanoyl or $C_3$–$C_5$alkenoyl and $R_{22}$ is $C_2$–$C_3$alkenyl.

The compounds of the formula Ia in which n is 2 are also preferred.

In general, the compounds of the formula I and Ia can be prepared by introducing the radical $R_7$ into the p-hydroxyl group in a compound of the formula II

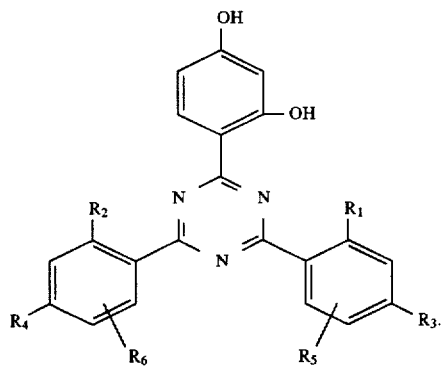

The compounds of the formula II are known compounds and can be prepared by a Friedel-Crafts reaction between cyanuric chloride and 1 mole of an aromatic compound of the formula

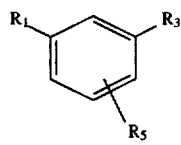

and 1 mole of an aromatic compound of the formula

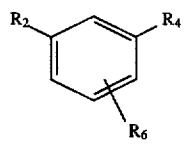

and 1 mole of resorcinol, as described, for example, in Swiss Patent 480,091 or in Swiss Patent 484,695 or in U.S. Pat. No. 3,244,708.

The conversion of II into I can be effected by various processes known per se, depending on the nature of the radical $R_7$. If $R_7$ is substituted alkyl, alkenyl, glycidyl, phenylalkyl, —CO—R$_{12}$, —SO$_2$—R$_{13}$, alkylene, alkenylene, xylylene or —COR$_{16}$CO—, the compound II or an alkali metal salt thereof can be reacted with a halogen compound of the formula Hal-R$_7$ or Hal-R$_7$-Hal in which Hal is chlorine, bromine or iodine, in particular with the compounds Cl—R$_7$ and Cl—R$_7$—Cl.

If $R_7$ is a group

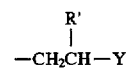

in which R' is hydrogen or CH$_3$ and Y is —COOR$_8$, —CONH$_2$, —CONHR$_9$, —CON(R$_9$)(R$_{10}$) or —CN, the compounds can be prepared by teacring a compound of the formula II with a compound of the formula

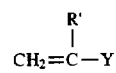

in the manner of a so-called Michael addition reaction.

If $R_7$ is a group —CH$_2$CH(OH)—W in which W is alkyl, phenyl, phenylalkyl or —CH$_2$OR$_{21}$, such compounds can be prepared by reacting a compound of the formula II with an epoxide of the formula

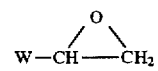

Analogously, compounds of the formula I in which n is 2 and $R_7$ is a group —CH$_2$CH(OH)CH$_2$O—R$_{15}$—OCH$_2$CH(OH)CH$_2$—, can be prepared by reacting 2 moles of a compound II and 1 mole of a bis-glycidyl ether of the formula

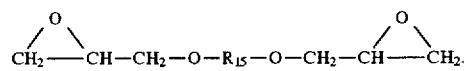

Compounds of the formula I in which $R_7$ is cyclohexyl substituted by OH can be prepared by reaction of H with cyclohexene oxide.

Compounds of the formula I in which n is 2 and $R_7$ is —CO—NH—R$_{17}$—NH—CO— can be prepared by reacting 2 moles of a compound of the formula II with 1 mole of a diisocyanate OCN—R$_{17}$—NCO. Compounds of the formula I in which n is 2 and $R_7$ is a group —CH$_2$CH(OH)CH$_2$— can be prepared by reacting 2 moles of a compound II with 1 mole of epichlorohydrin.

Compounds of formula I or Ia wherein n is 1 and $R_7$ is a group

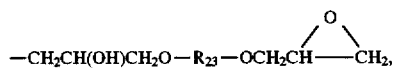

or a group —CO—R$_{24}$—COOH or —CONH—R$_{17}$—NCO can be prepared from II by reaction with one molar equivalent of a compound

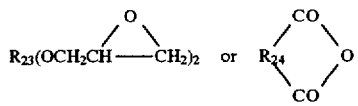

or OCN—R$_{17}$—NCO respectively.

It is also possible to convert a compound of the formula I into another compound of the formula I. For example, a hydroxyalkyl or aminoalkyl radical $R_7$ can be converted by acylation with $R_{11}COCl$ into the corresponding acyloxy or acylamino derivative.

Or a cyanoalkyl radical $R_7$ can be converted by reduction into an aminoalkyl radical. Compounds in which $R_7$ is alkyl which is substituted by —$COOR_8$ can be transesterified with another alcohol or polyol.

The methods required for the individual stages of the synthesis are known to those skilled in the art; some of them are described in greater detail in the examples which follow later.

The polyalkylpiperidines used as the component (a) preferably contain at least one group of the formula

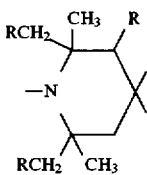

in which R is hydrogen or methyl. R is preferably hydrogen. These are derivatives of polyalkylpiperidines, in particular of 2,2,6,6-tetramethylpiperidine. These compounds preferably carry one or two polar substituents or a polar spiro ring system in the 4-position of the piperidine ring. These compounds can be low-molecular or oligomeric or polymeric compounds.

The following classes of polyalkylpiperidines are of particular importance.

a) Compounds of the formula III

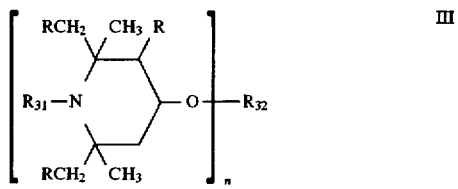

in which n is a number from 1 to 4, R is hydrogen or methyl, $R_{31}$ is hydrogen, amine oxide, hydroxyl, $C_1$–$C_{12}$alkyl, $C_3$–$C_8$alkenyl, $C_3$–$C_8$alkinyl, $C_{7-1}$–$C_{12}$aralkyl, $C_1$–$C_{18}$alkoxy, $C_5$–$C_8$cycloalkoxy, $C_7$–$C_9$phenylalkoxy, $C_1$–$C_8$alkanoyl, $C_3$–$C_5$alkenoyl, $C_1$–$C_{18}$alkanoyloxy, benzyloxy, glycidyl or a group —$CH_2CH(OH)$—Z, in which Z is hydrogen, methyl or phenyl, $R_{31}$ being preferably H, $C_1$–$C_4$alkyl, allyl, benzyl, acetyl or acryloyl, and, if n is 1, $R_{32}$ is hydrogen, $C_1$–$C_{18}$alkyl which can be interrupted by one or more oxygen atoms, cyanoethyl, benzyl, glycidyl, a monovalent radical of an aliphatic, cycloaliphatic, araliphatic, unsaturated or aromatic carboxylic acid, carbamic acid or an acid containing phosphorus or a monovalent silyl radical, preferably a radical of an aliphatic carboxylic acid having 2 to 18 C atoms, a cycloaliphatic carboxylic acid having 7 to 15 C atoms, an $\alpha,\beta$-unsaturated carboxylic acid having 3 to 5 C atoms or an aromatic carboxylic acid having 7 to 15 C atoms, or, if n is 2, is $C_1$–$C_{12}$alkylene, $C_4$–$C_{12}$alkenylene, xylylene, a divalent radical of an aliphatic, cycloaliphatic, araliphatic or aromatic dicarboxylic acid, dicarbamic acid, or acid containing phosphorus, or a divalent silyl radical, preferably a radical of an aliphatic dicarboxylic acid having 2 to 36 C atoms, a cycloaliphatic or aromatic dicarboxylic acid having 8–14 C atoms or an aliphatic, cycloaliphatic or aromatic dicarbamic acid having 8–14 C atoms, or, if n is 3, is a trivalent radical of an aliphatic, cycloaliphatic or aromatic tricarboxylic acid, an aromatic tricarbamic acid or an acid containing phosphorus, or a trivalent silyl radical, and, if n is 4, is a tetravalent radical of an aliphatic, cycloaliphatic or aromatic tetracarboxylic acid.

Examples of possible $C_1$–$C_{12}$alkyl substituents are methyl, ethyl, n-propyl, n-butyl, sec-butyl, tert-butyl, n-hexyl, n-octyl, 2-ethylhexyl, n-nonyl, n-decyl, n-undecyl or n-dodecyl.

As $C_1$–$C_{18}$alkyl, $R_{31}$ or $R_{32}$ can be the groups defined above and additionally, for example, n-tridecyl, n-tetradecyl, n-hexadecyl or n-octadecyl.

As $C_3$–$C_8$alkenyl, $R_{31}$ can, for example, be 1-propenyl, allyl, methallyl, 2-butenyl, 2-pentenyl, 2-hexenyl, 2-octenyl, 4-tert-butyl-2-butenyl.

As $C_3$–$C_8$alkenyl, $R_{31}$ is preferably propargyl.

As $C_7$–$C_{12}$aralkyl, $R_{31}$ is especially phenethyl and, in particular, benzyl.

Examples of $R_{31}$ as $C_1$–$C_8$alkanoyl are formyl, propionyl, butyryl or octanoyl, but preferably acetyl, and examples of $R_{21}$ as $C_3$–$C_5$alkenoyl are especially acryloyl.

Examples of $R_{31}$ as $C_1$–$C_{18}$alkoxy are hexyloxy, heptyloxy, octyloxy or decyloxy. As cycloalkoxy, $R_{31}$ is preferably cyclohexyloxy. As phenylalkoxy, $R_{31}$ is preferably benzyloxy. Examples of $R_{31}$ as alkanoyloxy are acetoxy, butyroyloxy, hexanoyloxy, octanoyloxy, decanoyloxy or stearoyloxy.

Examples of $R_{32}$ as a monovalent radical of a carboxylic acid are a radical of acetic acid, caproic acid, stearic acid, acrylic acid, methacrylic acid, benzoic acid or β-(3,5-di-tert-butyl-4-hydroxyphenyl)-propionic acid.

Examples of $R_{32}$ as a divalent radical of a dicarboxylic acid are a radical of malonic acid, succinic acid, glutaric acid, adipic acid, suberic acid, sebacic acid, maleic acid, itaconic acid, phthalic acid, dibutylmalonic acid, dibenzylmalonic acid, butyl-(3,5-di-tert-butyl-4-hydroxybenzyl)-malonic acid or bicycloheptenedicarboxylic acid.

Examples of $R_{32}$ as a trivalent radical of a tricarboxylic acid are a radical of trimellitic acid, citric acid or nitrilocriacetic acid.

Examples of $R_{32}$ as a tetravalent radical of a tetracarboxylic acid are the tetravalent radical of butane-1,2,3,4-tetracarboxylic acid or pyromellitic acid.

Examples of $R_{32}$ as a divalent radical of a dicarbamic acid are a radical of hexamethylenedicarbamic acid or 2,4-toluylenedicarbamic acid.

Preferred compounds of the formula III are those in which R is hydrogen, $R_{31}$ is hydrogen or methyl, n is 1 and $R_{32}$ is $C_1$–$C_{18}$alkyl, or n is 2 and $R_{32}$ is the diacyl radical of an aliphatic dicarboxylic acid having 4–12 C atoms.

The following compounds are examples of polyalkylpiperidine compounds of this class:

1) 4-Hydroxy-2,2,6,6-tetramethylpiperidine,
2) 1-Allyl-4-hydroxy-2,2,6,6-tetramethylpiperidine,
3) 1-Benzyl-4-hydroxy-2,2,6,6-tetramethylpiperidine,
4) 1-(4-tert-Butyl-2-butenyl)-4-hydroxy-2,2,6,6-tetramethylpiperidine,
5) 4-Stearoyloxy-2,2,6,6-tetramethylpiperidine,
6) 1-Ethyl-4-salicyloyloxy-2,2,6,6-tetramethylpiperidine,
7) 4-Methacryloyloxy-1,2,2,6,6-pentamethylpiperidine,
8) 1,2,2,6,6-Pentamethylpiperidin-4-yl β-(3,5-di-tert-butyl-4-hydroxyphenyl)-propionate,
9) Di-(1-benzyl-2,2,6,6-tetramethylpiperidin-4-yl) maleinate,
10) Di-(2,2,6,6-tetramethylpiperidin-4-yl) succinate,
11) Di-(2,2,6,6-tetramethylpiperidin-4-yl) glutarate,
12) Di-(2,2,6,6-tetramethylpiperidin-4-yl) adipate,
13) Di-(2,2,6,6-tetramethylpiperidin-4-yl) sebacate,
14) Di-(1,2,2,6,6-pentamethylpiperidin-4-yl) sebacate, 15) Di-(1,2,3,6-tetramethyl-2,6-diethyl-piperidin-4-yl) sebacate.
16) Di-(1-allyl-2,2,6,6-tetramethylpiperidin-4-yl) phthalate.
17) 1-Hydroxy-4-β-cyanoethyloxy-2,2,6,6-tetramethylpiperidine.
18) 1-Acetyl-2,2,6,6-tetramethylpiperidin-4-yl acetate.
19) Tri—(2,2,6,6-tetramethylpiperidin-4-yl) trimellitate.
20) 1-Acryloyl-4-benzyloxy-2,2,6,6-tetramethylpiperidine.
21) Di-(2,2,6,6-tetramethylpiperidin-4-yl) diethylmalonate.
22) Di-(1,2,2,6,6-pentamethylpiperidin-4-yl) dibutylmalonate.
23) Di-(1,2,2,6,6-pentamethylpiperidin-4-yl)butyl-(3,5-di-tert-butyl-4-hydroxybenzyl)-malonate.
24) Di-(1-octyloxy-2,2,6,6-tetramethylpiperidin-4-yl) sebacate.
25) Di-(1-cyclhexyloxy-2,2,6,6-tetramethylpiperidin-4-yl) sebacate.
26) Hexane-1',6'-bis-(4-carbamoyloxy-1-n-butyl-2,2,6,6-tetramethylpiperidine).
27) Toluene-2',4'-bis-(4-carbamoyloxy-1-n-propyl-2,2,6,6-tetramethylpiperidine).
28) Tetra-(2,2,6,6-tetramethylpiperidin-4-yl)butane-1,2,3,4-tetracarboxylate.
29) Tetra-(1,2,2,6,6-pentamethylpiperidin-4-yl)butane-1,2,3,4-tetracarboxylate.
30) Tris-(1-propyl-2,2,6,6-tetramethylpiperidin-4-yl) phosphite.
31) Tris-(1-propyl-2,2,6,6-tetramethylpiperidin-4-yl) phosphate.
32) Phenyl-[bis-(1,2,2,6,6-pentamethylpiperidin-4-yl)] phosphonate.
33) 4-Hydroxy-1,2,2,6,6-pentamethylpiperidine.
34) 4-Hydroxy-N-hydroxyethyl-2,2,6,6-tetramethylpiperidine.
35) 4-Hydroxy-N-(2-hydroxypropyl)-2,2,6,6-tetramethylpiperidine.
36) 1-Glycidyl-4-hydroxy-2,2,6,6-tetramethylpiperidine.

b) Compounds of the formula IV

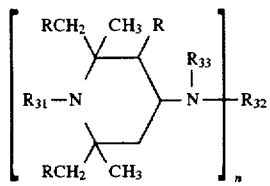

in which n is the number 1 or 2, R and $R_{31}$ are as defined under a), $R_{33}$ is hydrogen, $C_1$–$C_{12}$alkyl, $C_2$–$C_5$hydroxyalkyl, $C_5$–$C_7$cycloalkyl, $C_7$–$C_8$aralkyl, $C_2$–$C_{18}$alkanoyl, $C_3$–$C_5$alkenoyl, benzoyl or a group of the formula

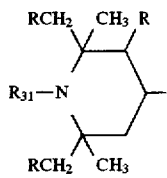

and, if n is 1, $R_{34}$ is hydrogen, $C_1$–$C_{18}$alkyl, $C_3$–$C_8$alkenyl, $C_5$–$C_7$cycloalkyl, $C_1$–$C_4$alkyl which is substituted by a hydroxyl, cyano, alkoxycarbonyl or carbamide group, glycidyl or a group of the formula —$CH_2$—$CH(OH)$—Z or of the formula —CONH—Z in which Z is hydrogen, methyl or phenyl or $R_{34}$ is a group —CO—CO—NH—($C_1$–$C_{18}$alkyl); or, if n is 2, $R_{34}$ is $C_2$–$C_{12}$alkylene, $C_6$–$C_{12}$arylene, xylylene, a —$CH_2$—$CH(OH)$—$CH_2$— group or a group —$CH_2$—$CH(OH)$—$CH_2$—O—D—O— in which D is $C_2$–$C_{10}$alkylene, $C_6$–$C_{15}$arylene or $C_6$–$C_{12}$-cycloalkylene or, provided that $R_{33}$ is not alkanoyl, alkenoyl or benzoyl, $R_{34}$ can also be a divalent radical of an aliphatic, cycloaliphatic or aromatic dicarboxylic acid or dicarbamic acid or the group —CO—, or, if n is 1, $R_{33}$ and $R_{34}$ together can be the divalent radical of an aliphatic, cycloaliphatic or aromatic 1,2-dicarboxylic or 1,3-dicarboxylic acid.

Possible $C_1$–$C_{12}$alkyl or $C_1$–$C_{18}$alkyl substituents are as already defined under a).

Possible $C_5$–$C_7$cycloalkyl substituents are especially cyclohexyl.

As $C_7$–$C_8$aralkyl, $R_{33}$ is especially phenylethyl or, in particular, benzyl. As $C_2$–$C_5$hydroxyalkyl, $R_{33}$ is especially 2-hydroxyethyl or 2-hydroxypropyl.

Examples of $R_{33}$ as $C_2$–$C_{18}$alkanoyl are propionyl, butyryl, octanoyl, dodecanoyl, hexadecanoyl or octadecanoyl, but preferably acetyl, and examples of $R_{33}$ as $C_3$–$C_5$alkenoyl are especially acryloyl.

Examples of $R_{34}$ as $C_2$–$C_6$alkenyl are allyl, methallyl, 2-butenyl, 2-pentenyl, 2-hexenyl or 2-octenyl.

Examples of $R_{34}$ as $C_1$–$C_4$alkyl which is substituted by a hydroxyl, cyano, alkoxycarbonyl or carbamide group are 2-hydroxyethyl, 2-hydroxypropyl, 2-cyanoethyl, methoxycarbonylmethyl, 2-ethoxycarbonylethyl, 2-aminocarbonylpropyl or 2—(dimethylaminocarbonyl)-ethyl.

Examples of possible $C_2$–$C_{12}$alkylene substituents are ethylene, propylene, 2,2-dimethylpropylene, tetramethylene, hexamethylene, octamethylene, decamethylene or dodecamethylene.

Examples of possible $C_6$–$C_{15}$arylene substituents are o-, m- or p-phenylene, 1,4-naphthylene or 4,4'-biphenylene.

As $C_6$–$C_{12}$cycloalkylene, D is especially cyclohexylene.

Preferred compounds of the formula IV are those in which n is 1 or 2, R is hydrogen, $R_{31}$ is hydrogen or methyl, $R_{33}$ is hydrogen, $C_1$–$C_{12}$alkyl or a group of the formula

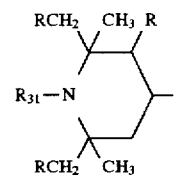

and, in the event that n=1, $R_{34}$ is hydrogen or $C_1$–$C_{12}$alkyl and, in the event that n=2, $R_{34}$ is $C_2$–$C_8$alkylene.

The following compounds are examples of polyalkylpiperidine compounds of this class:

37) N,N'-Bis-(2,2,6,6-tetramethylpiperidin-4-yl)-hexamethylene-1,6-diamine.
38) N,N'-Bis-(2,2,6,6-tetramethylpiperidin-4-yl)-hexamethylene-1,6-diacetamide.
39) Bis-(2,2,6,6-tetramethylpiperidin-4-yl)-amine.
40) 4-Benzoylamino-2,2,6,6-tetramethylpiperidine.
41) N,N'-Bis-(2,2,6,6-tetramethylpiperidin-4-yl)-N,N'-dibutyladipamide.
42) N,N'-Bis-(2,2,6,6-tetramethylpiperidin-4-yl)-N,N'-dicyclohexyl-2-hydroxypropylene-1,3-diamine.
43) N,N'-Bis-(2,2,6,6-tetramethylpiperidin-4-yl)-p-xylylenediamine.
44) N,N'-Bis-(2,2,6,6-tetramethylpiperidin-4-yl)-succindiamide.
45) N-(2,2,6,6-Tetramethylpiperidin-4-yl)-β-aminopropionic acid dodecyl ester.

46) The compound of the formula

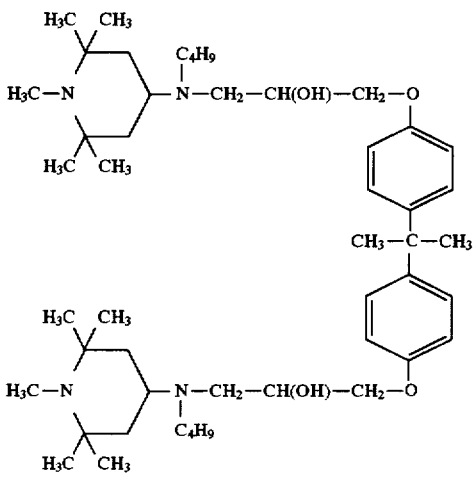

47) N-(1-Octyloxy-2,2,6,6-tetramethylpiperidin-4-yl)-N'-dodecyl-oxalamide
48) N-(2,2,6,6-Tetramethylpiperidin-4-yl)-α-dodecylsuccinimide.
49) 4-Methacrylamido-1,2,2,6,6-pentamethylpiperidine.

c) Compounds of the formula V.

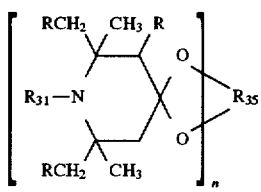

in which n is the number 1 or 2, R and $R_{31}$ are as defined under a) and, if n is 1, $R_{35}$ is $C_2$–$C_8$alkylene or $C_2$–$C_8$hydroxyalkylene or $C_4$–$C_{22}$acyloxyalkylene and, if n is 2, $R_{35}$ is the group (—$CH_2$)$_2$C($CH_2$—)$_2$.

Examples of $R_{35}$ as $C_2$–$C_8$alkylene or $C_2$–$C_8$hydroxyalkylene are ethylene, 1-methylethylene, propylene, 2-ethylpropylene or 2-ethyl-2-hydroxymethylpropylene.

An example of $R_{35}$ as $C_4$–$C_{22}$acyloxyalkylene is 2-ethyl-2-acetoxymethylpropylene.

The following compounds are examples of polyalkylpiperidine compounds of this class:

50) 9-Aza-8,8,10,10-tetramethyl-1,5-dioxaspiro[5.5]undecane.
51) 9-Aza-8,8,10,10-tetramethyl-3-ethyl-1,5-dioxaspiro[5.5]undecane.
52) 8-Aza-2,7,7,8,9,9-hexamethyl-1,4-dioxaspiro[4.5]decane.
53) 9-Aza-3-hydroxymethyl-3-ethyl-8,8,9,10,10-pentamethyl-1,5-dioxaspiro[5.5]undecane.
54) 9-Aza-3-ethyl-3-acetoxymethyl-9-acetyl-8,8,10,10-tetramethyl-1,5-dioxaspiro[5.5]undecane.
55) 2,2,6,6-Tetramethylpiperidin-4-spiro-2'-(1',3'-dioxane)-5'-spiro-5"-(1",3"-dioxane)-2"-spiro-4'"-(2'",2'",6'",6'"-tetramethylpiperidine).

d) Compounds of the formulae VIA, VIB and VIC

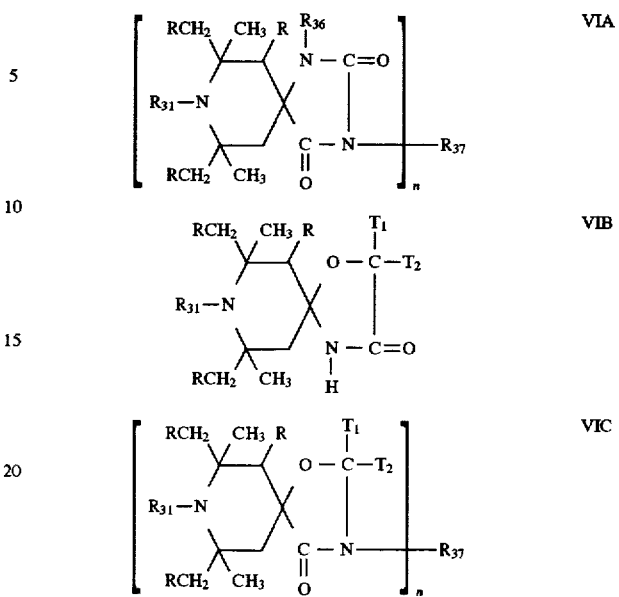

in which n is the number 1 or 2, R and $R_{31}$ are as defined under a), $R_{36}$ is hydrogen, $C_1$–$C_{12}$alkyl, allyl, benzyl, glycidyl or $C_2$–$C_6$alkoxyalkyl and, if n is 1, $R_{37}$ is hydrogen, $C_1$–$C_{12}$alkyl, $C_3$–$C_5$alkenyl, $C_7$–$C_9$aralkyl, $C_5$–$C_7$cycloalkyl, $C_2$–$C_4$hydroxyalkyl, $C_2$–$C_6$alkoxyalkyl, $C_6$–$C_{10}$aryl, glycidyl or a group of the formula —($CH_2$)$_p$—COO—Q or the formula —($CH_2$)$_p$—O—CO—Q in which p is 1 or 2 and Q is $C_1$–$C_4$alkyl or phenyl, or, if n is 2, $R_{36}$ is $C_2$–$C_{12}$alkylene, $C_4$–$C_{12}$alkenylene, $C_6$–$C_{12}$arylene, a group —$CH_2$—CH(OH)—$CH_2$—O—D—O—$CH_2$—CH(OH)—$CH_2$— in which D is $C_2$–$C_{10}$alkylene, $C_6$–$C_{15}$arylene or $C_6$–$C_{12}$cycloalkylene, or a group —$CH_2$CH(OZ')$CH_2$—(O$CH_2$—CH(OZ')$CH_2$)$_2$ in which Z' is hydrogen, $C_1$–$C_{18}$alkyl, allyl, benzyl, $C_2$–$C_{12}$alkanoyl or benzoyl. $T_1$ and $T_2$ independently of one another are hydrogen, $C_1$–$C_{18}$alkyl or $C_6$–$C_{10}$aryl or $C_7$–$C_9$aralkyl each of which is unsubstituted or substituted by halogen or $C_1$–$C_4$alkyl, or $T_1$ and $T_2$, together with the C atom linking them, form a $C_5$–$C_{12}$cycloalkane ring.

Examples of possible $C_1$–$C_{12}$alkyl substituents are methyl, ethyl, n-propyl, n-butyl, sec-butyl, tert-butyl, n-hexyl, n-octyl, 2-ethylhexyl, n-nonyl, n-decyl, n-undecyl or n-dodecyl.

Examples of possible $C_1$–$C_{18}$alkyl substituents can be the groups defined above and also, for example, n-tridecyl, n-tetradecyl, n-hexadecyl or n-octadecyl.

Examples of possible $C_2$–$C_6$alkoxyalkyl substituents are methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

Examples of $R_{37}$ as $C_3$–$C_5$alkenyl are 1-propenyl, allyl, methallyl, 2-butenyl or 2-pentenyl.

As $C_7$–$C_9$aralkyl, $R_{37}$, $T_1$ and $T_2$ are especially phenethyl or, in particular, benzyl. If $T_1$ abd $T_2$, together with the C atom, form a cycloalkane ring, this can, for example, be a cyclopentane, cyclohexane, cyclodecane or cyclododecane ring Examples of $R_{37}$ as $C_2$–$C_4$hydroxyalkyl are 2-hydroxyethyl, 2-hydroxypropyl, 2-hydroxybutyl or 4-hydroxybutyl.

As $C_6$–$C_{10}$aryl, $R_{37}$, $T_1$ and $T_2$ are especially phenyl, α-naphthyl or β-naphthyl each of which is unsubstituted or substituted by halogen or $C_1$–$C_4$alkyl.

Examples of $R_{37}$ as $C_2$–$C_{12}$alkylene are ethylene, propylene, 2,2-dimethylpropylene, tetramethylene, hexamethylene, octamethylene, decamethylene or dodecamethylene.

As $C_4$–$C_{12}$alkenylene, $R_{37}$ is especially 2-butenylene, 2-pentenylene or 3-hexenylene.

Examples of $R_{37}$ as $C_6$–$C_{12}$arylene are o-, m- or p-phenylene, 1,4-naphthylene or 4,4'-biphenylene.

Examples of Z' as $C_2$–$C_{12}$alkanoyl are propionyl, butyryl, octanoyl or dodecanoyl, but preferably acetyl.

As $C_2$–$C_{10}$alkylene, $C_6$–$C_{15}$arylene or $C_6$–$C_{12}$cycloalkylene, D is as defined under b).

The following compounds are examples of polyalkylpiperidine compounds of this class:

56) 3-Benzyl-1,3,8-triaza-7,7,9,9-tetramethylspiro[4.5]decane-2,4-dione.
57) 3-n-Octyl-1,3,8-triaza-7,7,9,9-tetramethylspiro[4.5]decane-2,4-dione.
58) 3-Allyl-1,3,8-triaza-1,7,7,9,9-pentamethylspiro[4.5]decane-2,4-dione.
59) 3-Glycidyl-1,3,8-triaza-7,7,8,9,9-pentamethylspiro[4.5]decane-2,4-dione.
60) 1,3,7,7,8,9,9-Heptamethyl-1,3,8-triazaspiro[4.5]decane-2,4-dione.
62) 2-Isopropyl-7,7,9,9-tetramethyl-1-oxa-3,8-diaza-4-oxospiro[4.5]decane.
62) 2,2-Dibutyl-7,7,9,9-tetramethyl-1-oxa-3,8-diaza-4-oxospiro[4.5]decane.
63) 2,2,4,4-Tetramethyl-7-oxa-3,20-diaza-21-oxo-dispiro[5.1.11.2]heneicosane.
64) 2-Butyl-7,7,9,9-tetramethyl-1-oxa-4,8-diaza-3-oxospiro[4.5]decane.
65) 8-Acetyl-3-dodecyl-1,3,8-triaza-7,7,9,9-tetramethylspiro[4.5]decane-2,4-dione or the compounds of the following formulae:

e) Compounds of the formula VII.

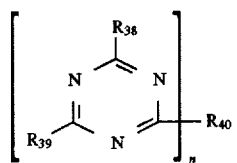

VII in which n is the number 1 or 2 and $R_{33}$ is a group of the formula

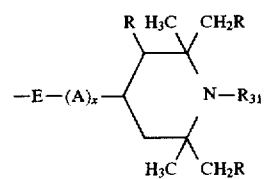

in which R and $R_{31}$ are as defined under a), E is —O— or —$NR_{41}$—, A is $C_2$–$C_6$alkylene or —$(CH_2)_3$—O— and x is the numbers 0 or 1, $R_{39}$ is identical with $R_{38}$ or is one of the groups —$NR_{41}R_{42}$, —$OR_{43}$, —$NHCH_2OR_{43}$ or —$N(CH_2OR_{43})_2$. $R_{40}$ is identical with $R_{38}$ or $R_{39}$, and, if n is 1, and if n is 2, is a group -E-B-E- in which B is $C_2$–$C_6$alkylene which can be interrupted by —$N(R_{41})$—, $R_{41}$ is $C_1$–$C_{12}$alkyl, cyclohexyl, benzyl or $C_1$–$C_4$hydroxyalkyl or a group of the formula 66) 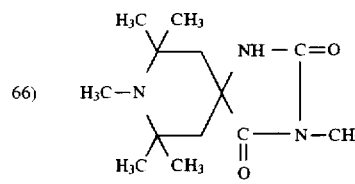

67) 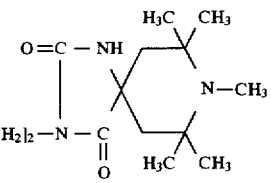

68) 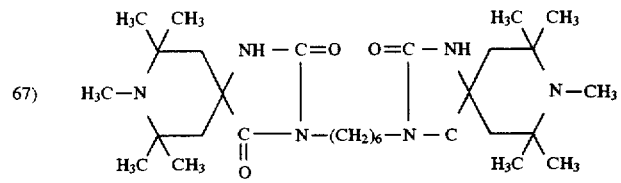

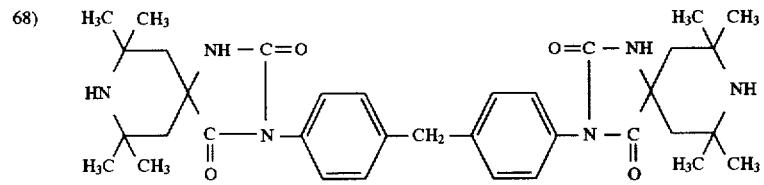

69) 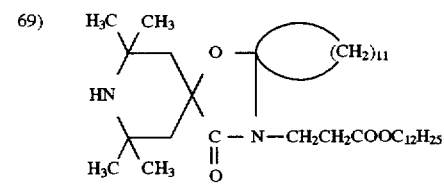

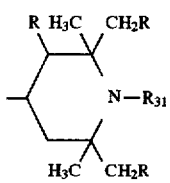

$R_{42}$ is $C_1$–$C_{12}$alkyl, cyclohexyl, benzyl or $C_1$–$C_4$hydroxyalkyl and $R_{43}$ is hydrogen, $C_1$–$C_{12}$alkyl or phenyl or $R_{41}$ and $R_{42}$ together are $C_4$–$C_5$alkylene or $C_4$–$C_5$oxaalkylene, for example

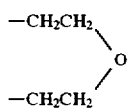

or a group of the formula

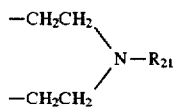

or $R_{41}$ and $R_{42}$ are each a group of the formula

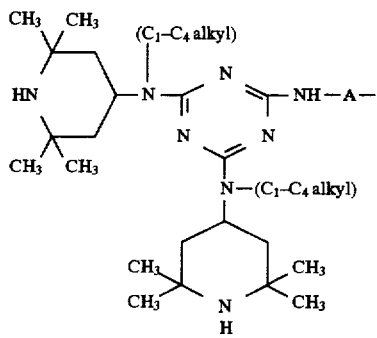

Examples of possible $C_1$–$C_{12}$alkyl substituents are methyl, ethyl, n-propyl, n-butyl, sec-butyl, tert-butyl, n-hexyl, n-octyl, 2-ethylhexyl, n-nonyl, n-decyl, n-undecyl or n-dodecyl.

Examples of possible $C_1$–$C_4$hydroxyalkyl substituents are 2-hydroxyethyl, 2-hydroxypropyl, 3-hydroxypropyl, 2-hydroxybutyl or 4-hydroxybutyl.

Examples of A as $C_2$–$C_6$alkylene are ethylene, propylene, 2,2-dimethylpropylene, tetramethylene or hexamethylene.

Examples of $R_{41}$ and $R_{42}$ together as $C_4$–$C_5$alkylene or oxaalkylene are tetramethylene, pentamethylene or 3-oxapentamethylene.

The compounds of the following formulae are examples of polyalkylpiperidine compounds of this class:

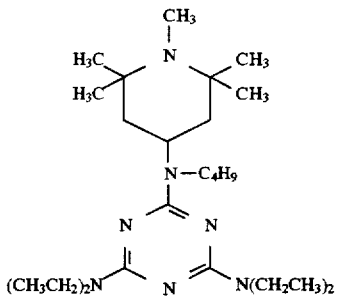

70)

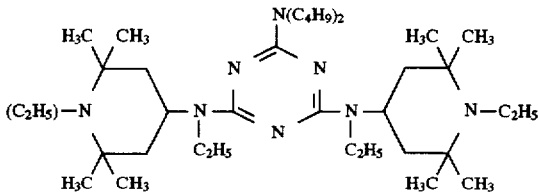

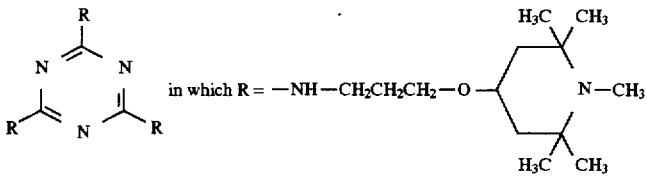

72)

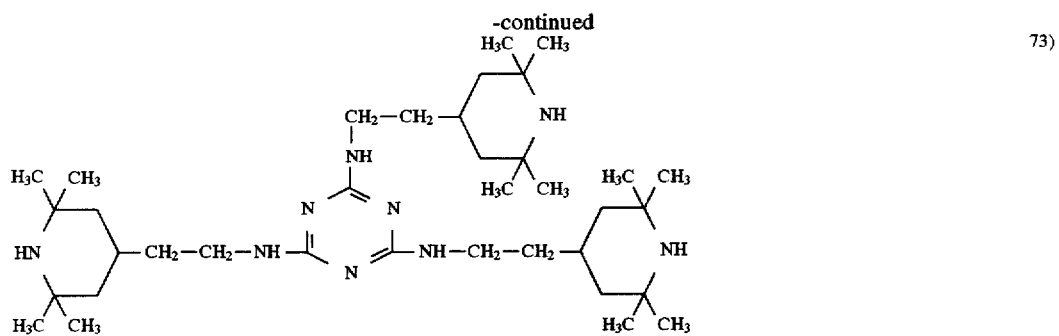
73)
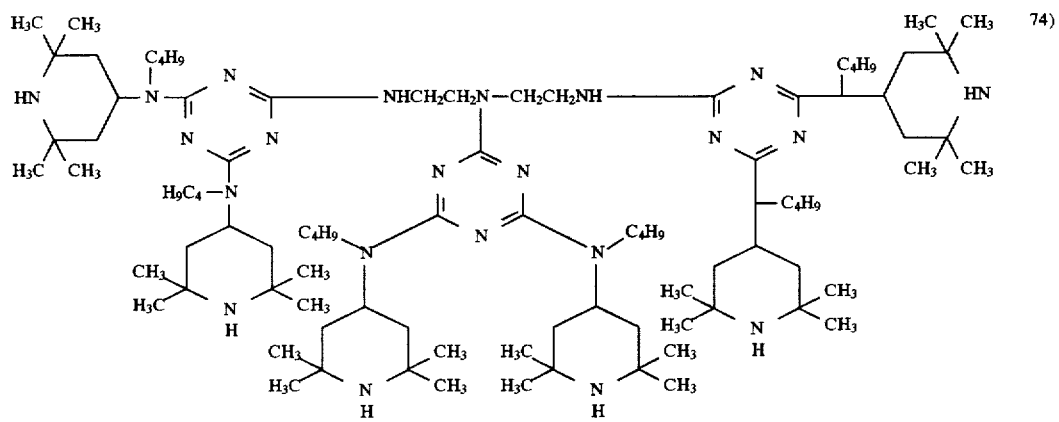
74)
75)
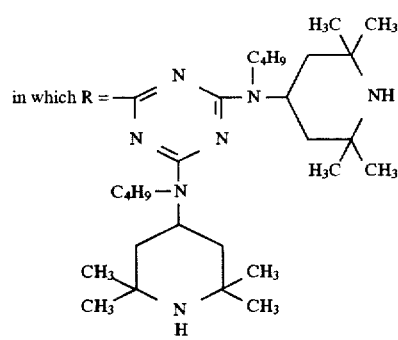
76)
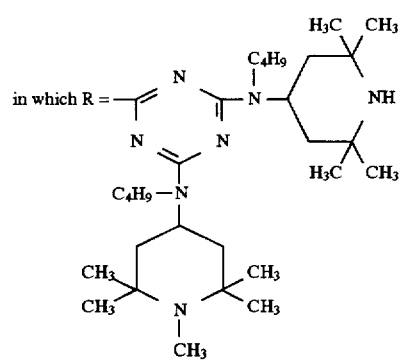
77)

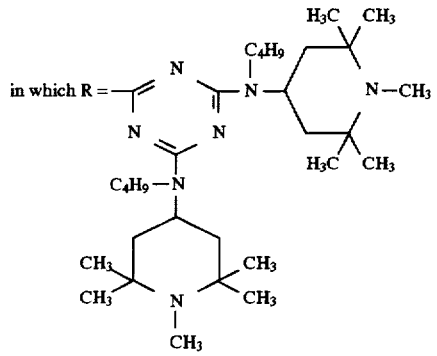

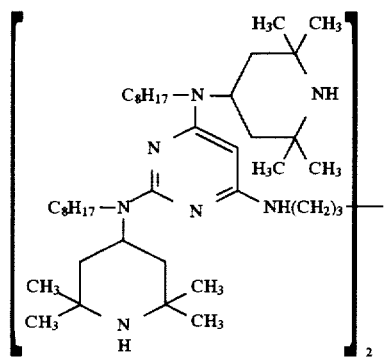
78)

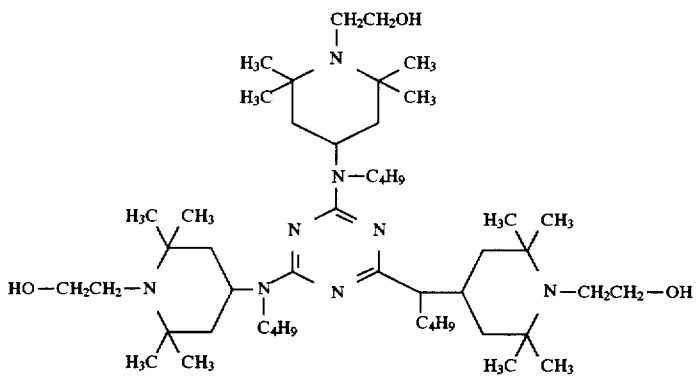
79)

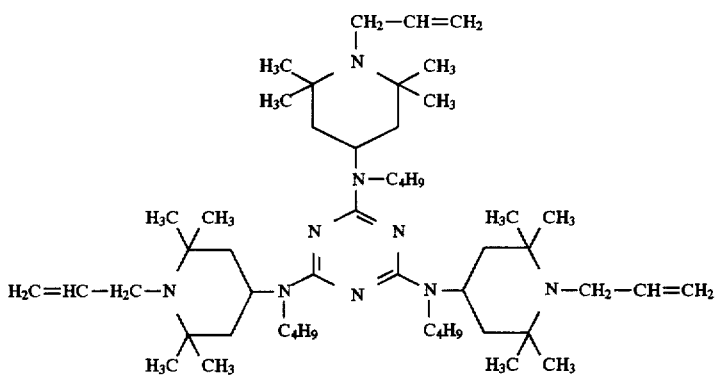
80)

f) Oligomeric or polymeric compounds in which the recurring structural unit contains a 2,2,6,6-tetraalkylpiperidine radical of the formula (I), in particular polyesters, polyethers, polyamides, polyamines, polyurethanes, polyureas, polyaminotriazines, poly (meth)acrylates, poly(meth)acrylamides and copolymers thereof containing radicals of this type.

The compounds of the following formulae in which m is a number from 2 to about 200 are examples of 2,2,6,6-polyalkylpiperidine light stabilizers of this class.

81) 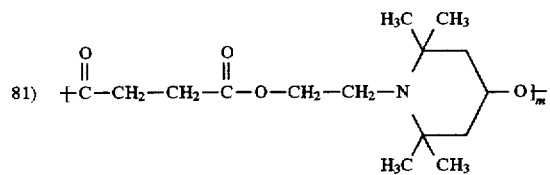
82) 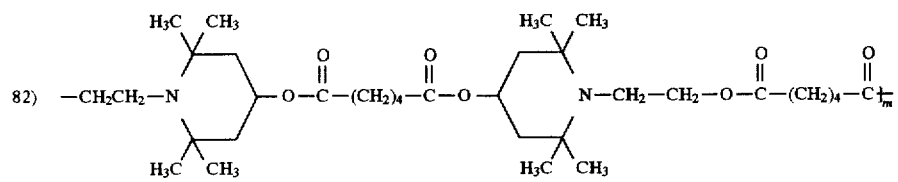
83) 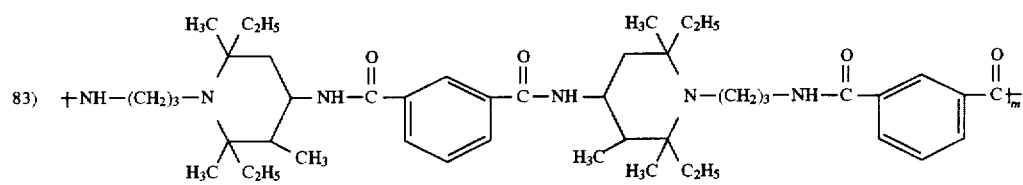
84) 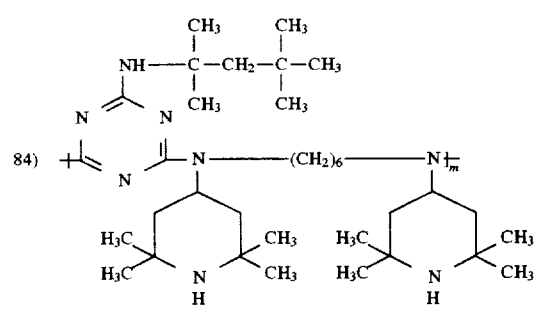
85) 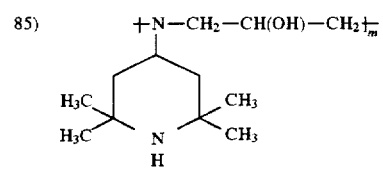
86) 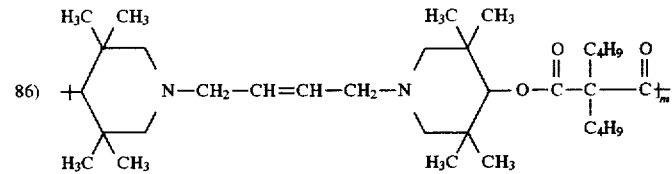
87) 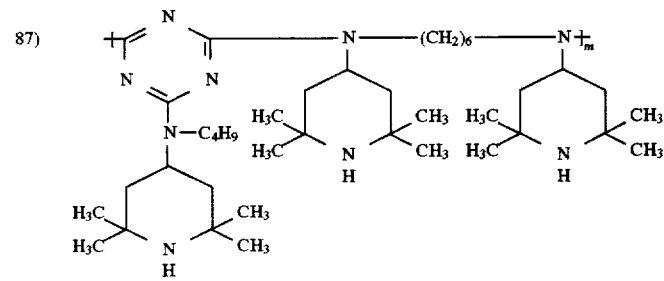
88) 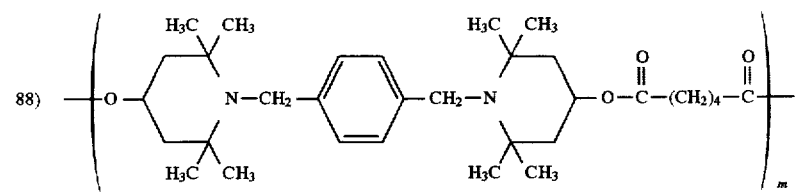

-continued

89) 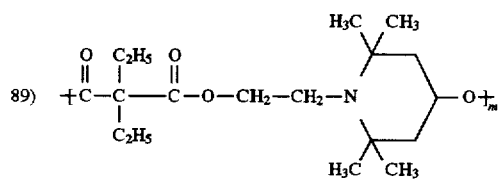

90) 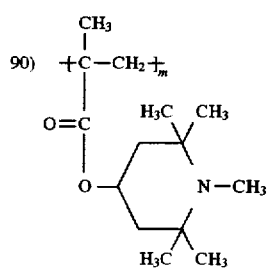

91) 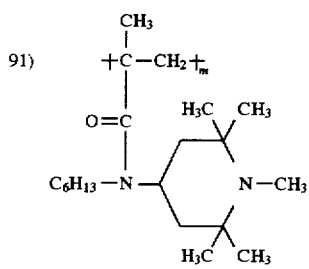

92) 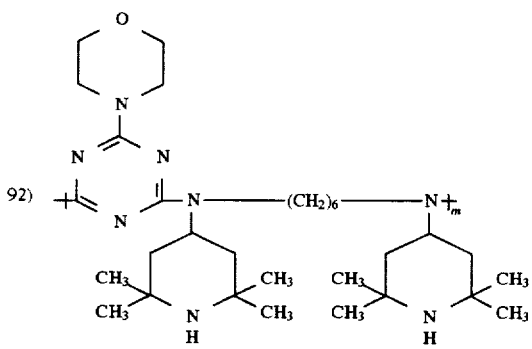

93) 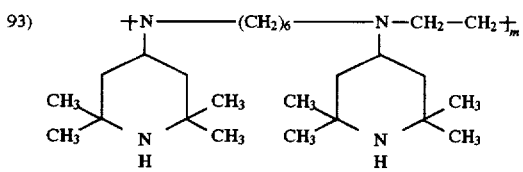

94) 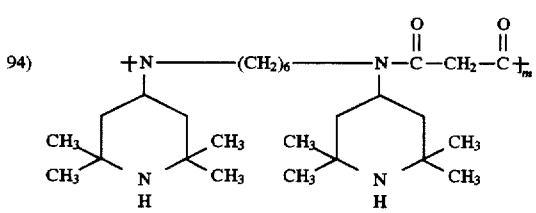

Of these classes of compounds, classes a), d), e) and f) are particularly suitable, in particular the Compounds Nos. 10, 13, 14, 23, 24, 28, 29, 45, 47, 48, 63, 65, 69, 75, 77, 81, 84, 92 and 93.

Examples of organic materials which can be stabilized with the mixture of (a) and (b) or with a compound of the formula Ia are fats, waxes, oils, cosmetics or photographic materials, but particularly organic polymers. The following classes are examples of polymers of this type:

1. Polymers of monoolefins and diolefins, for example polypropylene, polyisobutylene, polybut-1-ene, polymethylpent-1-ene, polyisoprene or polybutadiene, and polymerizates of cycloolefins, for example cyclopentene or norbornene; and also polyethylene (which can, if desired, be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene or of polypropylene with polyethylene (for example PP/HDPE or PP/LDPE) and mixtures of different types of polyethylene (for example LDPE/HDPE).

3. Copolymers of monoolefins and diolefins with one another or with other vinyl monomers, for example ethylene/propylene copolymers, linear low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under 1), for example polypropylene/ethylene/propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$), including hydrogenated modifications thereof (for example tackifying resins).

4. Polystyrene, poly-(p-methylstyrene) and poly-($\alpha$-methylstyrene).

5. Copolymers of styrene or $\alpha$-methyistyrene with dienes or acrylic derivatives, for example styrene/butadiene, styrene/acrylonitrile, styrene/alkyl methacrylate, styrene/butadiene/alkyl acrylate, styrene/maleic anhydride or styrene/acrylonitrile/methyl acrylate; mixtures of high impact resistance formed from styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene or $\alpha$-methylstyrene, for example styrene on polybutadiene, styrene on polybutadiene/styrene or polybutadiene/acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene, styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 5), such as are known, for example, as so-called ABS, MBS, ASA or AES polymers.

7. Halogen-containing polymers, for example polychloroprene, chlorinated rubber, chlorinated or chlorosulfonated polyethylene, copolymers of ethylene and chlodnated ethylene, epichlorohydrin homopolymers and copolymers, in particular polymers formed from halogen-containing vinyl compounds, for example polyvinyl chloride, polyvinylidene chloride, polyvinyl fluoride or polyvinylidene fluoride; and copolymers thereof, such as vinyl chloride/vinylidene chloride, vinyl chloride/vinyl acetate or vinylidene chloride/vinyl acetate.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned under 8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, stearate, benzoate or maleate, polyvinylbutyral, polyallyl phthalate or polyallylmelamine; and copolymers thereof with olefins mentioned in item 1.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene, and also polyoxymethylenes of this type containing comonomers, for example ethylene oxide, and polyacetals modified with thermoplastic polyurethanes, acrylates or MBS.

13. Polyphenylene oxides and sulfides and mixtures thereof with styrene polymers or polyamides.

14. Polyurethanes derived from polyethers, polyesters and polybutadienes having terminal hydroxyl groups on the one hand and from aliphatic or aromatic polyisocyanates on the other hand, and also precursors thereof.

15. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12 or 4/6, polyamide 11, polyamide 12 and aromatic polyamides formed from m-xylene, aliamine and adipic acid; and polyamides prepared from hexamethylenediamine and isophthalic and/or terephthalic acid and, if appropriate, an elastomer as modifier, for example poly-2,4,4-trimethylhexamethyleneterephthalamide or poly-m-phenyleneisophthalamide. Block copolymers of the polyamides mentioned above with polyolefins, olefin copolymers, ionomers or chemically attached or grafted elastomers; or with polyethers, for example polyethylene glycol, polypropylene glycol or polytetramethylene glycol. Also polyamides or copolyamides modified with EPDM or ABS; and polyamides which have been condensed during processing ("RIM polyamide systems").

16. Polyureas, polyimides, polyamide-imides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates and block polyether esters derived from polyethers having hydroxyl end groups; and also polyesters modified with polycarbonates or MBS.

18. Polycarbonates and polyester carbonates.

19. Polysulfones, polyether sulfones and polyether ketones.

20. Crosslinked polymers derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins derived from copolyesters of saturated and unsaturated dicarboxylic acids with polyhydric alcohols, and also vinyl compounds as crosslinking agents, and also halogen-containing modifications thereof of low flammability.

23. Crosslinkable acrylic resins derived from substituted acrylic acid esters, for example from epoxyacrylates, urethane acrylates or polyester acrylates.

24. Alkyd resins, polyester resins and acrylate resins crosslinked with melamine resins, urea resins, polyisocyanates or epoxy resins.

25. Crosslinked epoxy resins derived from polyepoxides, for example from bis-glycidyl ethers or cycloaliphatic diepoxides.

26. Natural polymers, such as cellulose, natural rubber, gelatine and the polymer-homologously chemically modified derivatives thereof, such as cellulose acetates, propionates and butyrates or the cellulose ethers, such as methylcellulose; and also colophony resins and derivatives.

The use of the compounds according to the invention in coatings of all types is particularly preferred. These can be pigmented or unpigmented coatings or metal effect coatings. They can contain an organic solvent or can be solvent-free or can be aqueous coatings.

The coatings can contain, as a binder, at least one of the polymers listed above. The following are examples of coatings containing special binders:

1. Coatings based on cold-crosslinkable or hot-crosslinkable alkyd, acrylate, polyester, epoxy or melamine resins or mixtures of such resins, if desired with an added acid curing catalyst;

2. Two-component polyurethane coatings based on acrylate, polyester or polyether resins containing hydroxyl groups, and on aliphatic or aromatic polyisocyanates;

3. One-component polyurethane coatings based on masked polyisocyanates which are unmasked during baking;

4. Two-component coatings based on (poly)ketimines and aliphatic or aromatic polyisocyanates;

5. Two-component coatings based on (poly)ketimines and an unsaturated acrylate resin or a polyacetoacetate resin or a methyl methacrylamidoglycolate;

6. Two-component coatings based on polyacrylates and polyepoxides containing carboxyl or amino groups;

7. Two-component coatings based on acrylate resins containing anhydride groups, and on a polyhydroxyl or polyamino component;

8. Two-component coatings based on (poly)oxazolidines and acrylate resins containing anhydride groups, or unsaturated acrylate resins or aliphatic or aromatic polyisocyanates;

9. Two-component coatings based on unsaturated polyacrylates and polymalonates;

10. Thermoplastic polyacrylate coatings based on thermoplastic acrylate resins or extraneously crosslinking acrylate resins in combination with etherified melamine resins;

11. Coating systems based on siloxane-modified or silane-modified or fluorine-modified acrylate resins.

The coatings can also be radiation-curable. In this case the binder is composed of monomeric or oligomeric compounds which contain ethylenic double bonds and are converted into a crosslinked, high-molecular form by irradiation with actinic light or with electron beams. In most cases the binder is a mixture of such compounds. In radiation-curable coatings the compounds of formula I can be used also in absence of a sterically hindered amine.

The coatings can be applied as one-coat or two-coat systems, it being preferable to add the stabilizers according to the invention to the unpigmented top coat.

The coatings can be applied to the substrates (metal, plastic, wood, etc.) by the customary processes, for example by brushing, spraying, curtain-coating, dipping or electrophoresis.

The amount of (a) and (b) added depends on the substrate and the requirements for its stability. In general, 0.01 to 5% by weight, in particular 0.02 to 2% by weight, of the component (a) and 0.02 to 5% by weight, in particular 0.05 to 3% by weight, of the component (b) are added, relative to the polymer.

The two components can be added on their own or as a mixture. Addition is preferably carried out before or during the shaping of the polymer. It can also be carried out as early as the preparation of the polymer, for example before or during polymerization.

The compounds of the formula Ia can also be used on their own, ie. without a sterically hindered amine, for stabilizing organic polymers. In this case 0.01 to 10% by weight, for example, preferably 0.05 to 5% by weight, of a compound of the formula Ia is added to the polymer. The use of compounds of the formula Ia as a stabilizer for polycarbonates is of particular interest.

In addition to the stabilizers, according to the invention, of the formula Ia or the stabilizer combination (a)+(b), it is also possible to add other stabilizers to the polymer. The following are examples of these:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-dioctadecyl-4-methylphenol-2,4,6-trimethylphenol, 2,6-di-tert-butyl-4-methoxymethylphenol and 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone and 2,6-diphenyl-4-octadecyloxyphenol.

1.3. Hydroxylated thiodiphenyl ethers, for example 2,2'-thiobis-(6-tert-butyl-4-methylphenol), 2,2'-thiobis-(4-octylphenol), 4,4'-thiobis-(6-tert-butyl-3-methylphenol), 4,4'-thiobis-(6-tert-butyl-2-methylphenol).

1.4. Alkylidene bisphenols, for example 2,2'-methylenebis-(6-tert-butyl-4-methylphenol), 2,2'-methylenebis-(6-tert-butyl-4-ethylphenol), 2,2'- methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-di-tert-butylphenol), 2,2'-ethylidenebis-(4,6-di-tert-butylphenol), 2,2'-ethylidenebis-(6-tert-butyl-4-isobutylphenol), 2,2'-methylenebis-[6-(α-methylbenzyl)-4-nonylphenol], 2,2'-methylenebis-[6-(α,α-dimethylbenzyl)-4-nonylphenol], 4,4'-methylenebis-(2,6-di-tert-butylphenol), 4,4'-methylenebis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4-methylphenol, 1,1,3-tris-(5-tert-butyl-4-hydroxy-2-methylphenyl)-butane, 1,1-bis-(5-tert-butyl-4-hydroxy-2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene and bis-[2-(3'-tert-butyl-2-hydroxy-5'-methylbenzyl)-6-tert-butyl-4-methylphenyl] terephthalate.

1.5. Benzyl compounds, for example 1,3,5-tris-(3,5-di-tert-butyl-4-hydroxybenzyl)-2,4,6-trimethylbenzene, bis-(3,5-di-tert-butyl-4-hydroxybenzyl) sulfide, isooctyl 3,5-di-tert-butyl-4-hydroxybenzylmercaptoacetate, bis-(4-tert-butyl-3-hydroxy-2,6-dimethylbenzyl)-dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, the Ca salt of monoethyl 3,5-di-tert-butyl-4-hydroxybenzylphosphonate and 1,3,5-tris-(3,5-dicyclohexyl-4-hydroxybenzyl) isocyanurate.

1.6. Acylaminophenols, for example 4-hydroxylauranilide, 4-hydroxystearanilide, 2,4-bis-(octylmercapto)-6-(3,5-di-tert-butyl-4-hydroxyanilino)-s-triazine and octyl N-(3,5-di-tert-butyl-4-hydroxyphenyl)-carbamate.

1.7. Esters of β-(3,5-di-tert-butyl-4-hydroxyphenyl)-propionic acid, with monohydric or polyhydric alcohols, for example methanol, octadecanol, 1,6-hexanediol, neopentyl glycol, thiodiethylene glycol, diethylene glycol, triethylene glycol, pentacrythritol, tris-(hydroxyethyl) isocyanurate and N,N'-bis-(hydroxyethyl)oxamide.

1.8. Esters of β-(5-tert-butyl-4-hydroxy-3-methylphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and N,N'-bis-(hydroxyethyl)oxamide.

1.9. Esters of β-(3,5-dicyclohexyl-4-hydroxyphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate and N,N'-bis-(hydroxyethyl)oxamide.

1.10. Amides of β-(3,5-di-tert-butyl-4-hydroxyphenyl)-propionic acid, for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

2. UV Absorbers and Light Stabilizers 2.1.2-(2'-hydroxyphenyl)-benzotriazoles, for example the 5'-methyl-, 3',5'-di-tert-butyl- , 5'-tert-butyl-,5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, 3',5'-di-tert-amyl-, 3',5'-bis-(α,α-dimethylbenzyl)-derivative.

2.2.2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.3. Esters of unsubstituted or substituted benzoic acids, for example 4-tert-butylphenyl salicylate, phenyl salicylate, octylphenyl salicylate, dibenzoylresorcinol, bis-(4-tert-butylbenzoyl)-resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

2.5. Nickel compounds, for example nickel complexes of 2,2'-thiobis-[4-(1,1,3,3-tetramethylbutyl)-phenol], such as the 1:1 complex or the 1:2 complex, if appropriate with additional ligands, such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as the methyl or ethyl ester, nickel complexes of ketoximes, such as 2-hydroxy-4-methylphenyl undecyl ketoxime, or nickel complexes of 1-phenyl-4-lauroyl-5-hydroxypyrazole, if appropriate with additional ligands.

2.6. Oxamides, for example 4,4'-di-octyloxyoxanilide, 2,2'-di-octyloxy-5,5'-di-tert-butyloxanilide, 2,2'-di-dodecyloxy-5,5'-di-tert-butyloxanilide, 2-ethoxy-2'-ethyloxanilide, N,N'-bis-(3-dimethylanminopropyl)-oxalamide, 2-ethoxy-5-tert-butyl-2'-ethyloxanilide and a mixture thereof with 2-ethoxy-2'-ethyl-5,4'-di-tert-butyloxanilide or mixtures of o-methoxy- and p-methoxy-disubstituted oxanilides and of o-ethoxy- and p-ethoxy-disubstituted oxanilides.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole and bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythritol diphosphite, tris-(2,4-di-tert-butylphenyl) phosphite, diisodecyl pentaerythritol diphosphite, bis-(2,4-di-tert-butylphenyl) pentaerythritol diphosphite, tristearyl sorbitol triphosphate, tetrakis-(2,4-di-tert-butylphenyl) 4,4'-biphenylene diphosphonite and 3,9-bis-(2,4-di-tert-butylphenoxy)-2,4,8,10-tetraoxa-3,9-diphosphaspiro[5.5] undecane.

5. Compounds which destroy peroxides, for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide and pentaerythritol tetrakis-(β-dodecylmercapto)propionate.

6. Polyamide stabilizers, for example copper salts in combination with iodides and/or phosphorus compounds and salts of divalent manganese.

7. Basic co-stabilizers, for example melamine, polyvinylpyrrolidone, dicyandiamide, triallyl cyanurate, urea derivatives, hydrazine derivatives, amines, polyamides, polyurethanes, alkali and alkaline earth salts of higher fatty acids, for example Ca stearate, Zn stearate, Mg stearate, Na ricinoleate and K palmitate, antimony pyrocatecholate or tin pyrocatecholate.

8. PVC stabilizers, for example organotin compounds or salts of barium, cadmium, zinc and led.

Other materials such as are customary in the technology of plastics and paints can also be added. Examples of these are fillers and reinforcing agents, pigments, dyes, plasticizers, solvents, lubricants, flow-control agents, fluorescent brighteners, nucleating agents, antistatic agents or fire-retarding agents.

The invention also relates, therefore, to organic polymers containing, as stabilizers, a sterically hindered amine of the polyalkylpiperidine type and a hydroxyphenyltriazine of the formula I, and also to organic polymers containing a compound of the formula Ia as the stabilizer.

The polymers stabilized in this manner can be used in various shapes, for example as films, fibres, tapes, mouldings, profiles, latex, dispersions, paints or cements.

The following examples illustrate the invention in greater detail without intending to limit it to the examples. Pans and percentages are parts by weight and percentages by weight.

PREPARATION EXAMPLES

Example 1

23.8 g (0.06 mol) of 2-(2,4-dihydroxyphenyl)-4,6-bis-(2,4-dimethylphenyl)-1,3,5-triazine (prepared as described in U.S. Pat. No. 3,244,708 Example 16) are suspended in 300 ml of xylene. 12.1 g (0.09 mol) of 97% butyl glycidyl ether and 0.75 g (0.006 mol) of dimethylbenzylamine are added to this suspension, and the mixture is heated to reflux temperature. After a reaction time of 5 hours the clear, brownish solution is cooled and clarified by filtration through 100 g of silica gel. The yellow solution is evaporated and the residue is recrystallized from hexane/toluene. This gives 27.3 g of pale yellow crystals of 2-[2-hydroxy-4(3-butoxy-2-hydroxypropyloxy)-phenyl]-4,6-bis(2,4-dimethylphenyl)-1,3,5-triazin (=86% yield). Melting point: 80°–83° C. (Compound 1).

In analogous manner the compounds 2 to 28, listed in Table 1, are obtained from 2-(2,4-dihydroxyphenyl)-4,6-bis(2,4-dimethylphenyl)-1,3,5-triazine and an epoxy compound.

TABLE 1

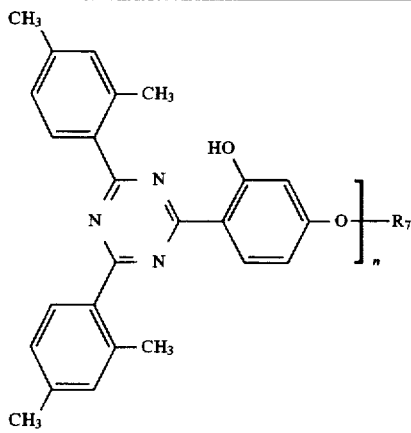

| Compound | n | $R_7$ | Physical data |
|---|---|---|---|
| 1 | 1 | —$CH_2CH(OH)CH_2OC_4H_9$ | m.p. 80–83° C. |
| 2 | 1 | —$CH_2CH(OH)CH_2OCOC(CH_3)=CH_2$ | m.p. 100–103° C. |
| 3 | 2 | —$CH_2CH(OH)CH_2O—(CH_2)_4—OCH_2CH(OH)CH_2—$ | m.p. 150–152° C. |
| 4 | 1 | —$CH_2CH(CH_2)_3CH_3$<br>\|<br>OH | m.p. 115–117° C. |
| 5 | 1 | —$CH_2CH(OH)CH_2—OH$ | m.p. 165–167° C. |
| 6 | 1 | —$CH_2CH(OH)CH_2—O—C_6H_5$ | m.p. 101–104° C. |
| 7 | 1 | —$CH_2CH(OH)CH_2—O—CH_2CH—C_4H_9$<br>\|<br>$C_2H_5$ | m.p. 75–77° C. |
| 8 | 1 | OH<br>\|<br>$CH_3(CH_2)_7CH—CH—(CH_2)_7COOC_8H_{17}$<br>\| | Oil<br>found:   calc.:<br>C: 75.6%  C: 75.9%<br>H: 9.2%   H: 9.1% |
| 9 | 2 | —$CH_2CH(OH)CH_2—O—C_6H_4—C(CH_3)_2—C_6H_4—O—CH_2CH(OH)CH_2—$ | m.p. 100–103° C. |
| 10 | 1 | —$CH_2CH(OH)(CH_2)_{11}CH_3$ | m.p. 102–104° C. |
| 11 | 1 | —$CH_2CH(OH)(CH_2)_7CH_3$ | m.p. 97–99° C. |

TABLE 1-continued

[Structure: triazine with two 2,4-dimethylphenyl groups connected via C=N linkages to a central triazine, connected to a 2-hydroxy-phenyl group with O—R$_7$ substituent, subscript n]

| Compound | n | R$_7$ | Physical data |
|---|---|---|---|
| 12 | 1 | —CH$_2$CH(OH)CH$_2$O—CH(CH$_2$OCH$_2$CH—CH$_2$)$_2$ with C(CH$_3$)$_2$ bridged dioxy group | Oil<br>found: C: 64.0%, H: 7.6%, N: 4.4%<br>calc.: C: 66.7%, H: 7.16%, N: 5.4% |
| 13 | 1 | —CH$_2$CH(OH)CH$_2$O—(CHCH$_2$O)$_r$—CH$_2$CH—CH$_2$ (with CH$_3$ branch, epoxide end)<br>r = 10–14 | Oil<br>found: N: 3.75%<br>calc.: N: 3.43% |
| 14 | 2 | —CH$_2$CH(OH)CH$_2$O—(CHCH$_2$O)$_r$—CH$_2$CH(OH)CH$_2$— (with CH$_3$ branch)<br>r = 10–14 | Oil<br>found: N: 5.17%<br>calc.: N: 5.18% |
| 15 | 1 | —CH$_2$CH(OH)CH$_2$OCOC$_9$H$_{19}$ | Oil<br>found: N: 6.3%<br>calc.: N: 6.7% |
| 16 | 1 | [cyclohexyl with HO substituent] | m.p. 152–155° C. |
| 17 | 1 | —CH$_2$CH(OH)CH$_2$O(C$_{13}$H$_{27}$ to C$_{15}$H$_{31}$) | Oil<br>MS, NMR |
| 18 | 1 | —CH$_2$CH(OH)CH$_2$O(C$_{12}$H$_{25}$ to C$_{14}$H$_{29}$) | Oil<br>MS, NMR |
| 19 | 2 | —CH$_2$CH(OH)CH$_2$OCH$_2$C(CH$_3$)$_2$CH$_2$OCH$_2$CH(OH)CH$_2$— | Resin<br>found: C = 71.3%, H = 6.6%<br>calc.: C = 71.4%, H = 6.6% |
| 20 | 1 | —CH$_2$CH(OH)CH$_2$OCOC$_{10}$H$_{21}$-tert. | Resin<br>MS, NMR |
| 21 | 1 | —CH$_2$CH(OH)CH$_2$OCH$_2$CH=CH$_2$ | m.p. 94–95° C. |
| 22 | 1 | —CH$_2$CH(OH)CH$_3$ | m.p. 151–153° C. |
| 23 | 1 | —CH$_2$CH(OH)CH$_2$O—[furyl] | m.p. 99–101° C. |
| 24 | 2 | [two cyclohexyl rings with OH, connected by —CO—O—CH$_2$—] | Resin<br>found: N = 8.2%<br>calc.: N = 8.3% |

Example 2

22.1 g (0.05 mol) of 2-(2-hydroxy-4-hydroxyethoxyphenyl)-4,6-bis(2,4-dimethylphenyl)-1,3,5-triazine (prepared as described in U.S. Pat. No. 3,244,708, Example 18), are dissolved in 300 ml of tetrahydrofurane at 40° C. and 21 ml (0.15 mol) of triethylamine are added. A solution of 5.05 ml (0.053 mol) of acrylic acid chloride in 20 ml THF is added dropwise with stirring and with cooling the reaction mixture to 25°–30° C. After further stirring of two hours the precipitated ammonium salt is filtered off, the filtrate is evaporated and the residue recrystallized from toluene-hexane mixture to obtain 22 g (88.7% yield) of 2-(2-hydroxy-4-acryloyloxyethoxy-phenyl)-4,6-bis(2,4-dimethylphenyl)-1,3,5-triazine as slightly yellow crystals (compound No. 25), m.p. 128°–129° C.

In analogous manner the compounds No. 26 and 27 were prepared.

| Compound | n | $R_7$ | Phys. data |
|---|---|---|---|
| 25 | 1 | —CH$_2$CH$_2$OCOCH=CH$_2$ | m.p. 128–129° C. |
| 26 | 1 | —CH$_2$CH(CH$_3$)OCOCH=CH$_2$ | m.p. 128–129° C. |
| 27 | 1 | —CH$_2$CH$_2$OCOCH(CH$_3$)=CH$_2$ | m.p. 128–129° C. |

Example 3

20 g (0.04 mol) of 2-(2-hydroxy-4-ethoxycarbonylmethoxyphenyl)-4,6-bis-(2,4-dimethylphenyl)-1,3,5-triazine (prepared as described in U.S. Pat. No. 3,244,708, Example 19), are dissolved in 100 ml of toluene, and 5 g (0.048 mol) of 2-methylpentanol and 0.5 g of dibutyltin oxide as catalyst are added, and the mixture is heated to reflux temperature. In the course of this a toluene/ethanol mixture is distilled off. The toluene is replenished dropwise from a dropping funnel. The transesterification reaction is complete after 2 hours. The solution is cooled and filtered through 80 g of silica gel and is then evaporated. The residue is recrystallized from ethanol. This gives 14 g of the compound 28 (see Table 2). Melting point: 87°–89° C.

Compounds 29 to 37 are obtained analogously by transesterification with the corresponding alcohols.

TABLE 2

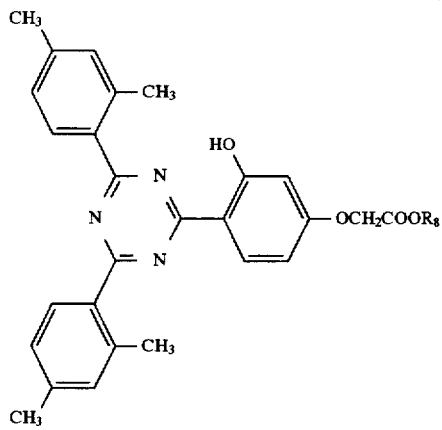

| Compound | $R_8$ | Physical data | | | |
|---|---|---|---|---|---|
| 28 | —CH$_2$CHCH$_2$CH$_2$CH$_3$<br>        \|<br>       CH$_3$ | m.p. 87–89° C. | | | |
| 29 | —CH$_2$CH$_2$CH$_2$CH$_3$ | m.p. 136–138° C. | | | |
| 30 | —C$_8$H$_{17}$ (isomer mixture) | Waxlike<br>calcd.<br>found | C 74.05%<br>C 73.98% | H 7.28%<br>H 7.36% | N 7.4%<br>N 7.3% |
| 31 | —(CH$_2$CH$_2$O)$_n$—H  n ≈ 7 | Oil<br>calcd.<br>found | C 64.47%<br>C 64.75% | H 6.99%<br>H 7.00% | N 5.50%<br>N 5.72% |
| 32 | —C$_{10}$H$_{21}$ (isomer mixture) | Waxlike<br>calcd.<br>found | C 74.59%<br>C 74.76% | H 7.61%<br>H 7.73% | N 7.05%<br>N 6.89% |
| 33 | —CH$_2$CH—OCH$_2$CH—OCH$_2$CH—CH$_3$<br>    \|          \|          \|<br>  CH$_3$     CH$_3$     CH$_3$ | Resin<br>calcd.<br>found | C 70.45%<br>C 70.12% | H 7.06%<br>H 7.02% | N 6.85%<br>N 6.84% |
| 34 | —CH$_2$—P(OC$_4$H$_9$)$_2$<br>       \|\|<br>       O | m.p. 75–78° C. | | | |
| 35 | —(CH$_2$)$_8$CH=CH—(CH$_2$)$_7$—CH$_3$ | Waxlike<br>calcd. | C 76.96% | H 8.42% | N 5.95% |

TABLE 2-continued

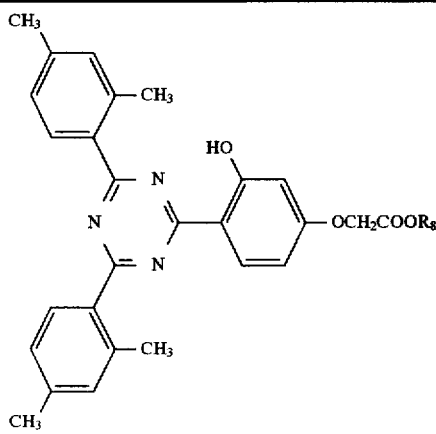

| Compound | R₈ | Physical data | | | |
|---|---|---|---|---|---|
| 36 | —(CH₂)₂O(CH₂)₂OC₆H₁₃ | found Resin calcd. found | C 77.02% C 70.68% C 70.53% | H 8.47% H 7.37% H 7.49% | N 5.74% N 6.68% N 6.39% |
| 37 | —(CH₂CH₂O)$_n$—H  n = 9 | Resin calcd. found | C 63.44% C 63.54% | H 7.22% H 7.20% | N 4.93% N 5.01% |

Example 4

9.1 g (0.02 mol) of 2-(2-hydroxy-4-carboxymethoxyphenyl)-4,6-bis(2,4-dimethylphenyl)-1,3,5-triazine (prepared as described in U.S. Pat. No. 3,244,708, Example 16) are suspended in 40 ml of thionyl chloride, and 1 ml of DMF is added. The mixture is heated at reflux temperature for 2 hours. A clear yellow solution is formed with moderate evolution of gas. This solution is evaporated to give 9.5 g of [4-(4,6-di-2',4'-xylyl-s-triazin-2-yl)-3-hydroxyphenoxy]-acetyl chloride (Compound 38). This acid chloride is dissolved in 100 ml of toluene. 19.3 g (0.08 mol) of bis-(2-ethylhexyl)-amine are added dropwise at room temperature. The reaction proceeds exothermically from 22° C. to 40° C. The mixture is left for 1 hour at room temperature to complete the reaction. The product is then purified by column chromatography over silica gel. This gives approx. 5 g of a pale yellow, highly viscous oil, [4-(4,6-di-2',4'-xylyl-s-triazin-2-yl)-3-hydroxyphenoxy]-acetic acid bis-(2-ethylhexyl)-amide (Compound 39).

Calcd. C 76.07%, H 8.61%, N 8.25% Found. C 75.91%, H 8.46%, N 8.16%

Example 5

39.7 g (0.1 mol) of 2-(2,4-dihydroxyphenyl)-4,6-bis(2,4-dimethylphenyl)-1,3,5-triazine are dissolved in 250 ml of DMZF. 20.7 g of potassium carbonate are added to this brownish solution. An orange suspension is formed. 17 g (0.052 mol) of 1,12-dibromododecane are added and the mixture is heated at 100° C. The reaction is complete after 2 hours. The cooled reaction solution is then poured into 1.5 l of water, and the precipitate is filtered off and washed with 2-3 times 100–200 ml of H₂O. The crystals are then recrystallized from xylene. Melting point: 158°–163° C. (Compound 40).

Compounds 41 and 42 are obtained analogously, using 1,6-dibromohexane, 1,4-dichloro-2-butene and p-xylylenedibromid.

TABLE 3

| Compound | R₇ | Physical data |
|---|---|---|
| 40 | —(CH₂)₁₂— | m.p. 158–163° C. |
| 41 | —(CH₂)₆— | m.p. 203–205° C. |
| 42 | —CH₂—CH=CH—CH₂— | m.p. 230–235° C. |
| 43 | —CH₂—⟨phenyl⟩—CH₂— | m.p. 252–254° C. |

Example 6

20 g (0.05 mol) of 2-(2,4-dihydroxyphenyl)-4,6-bis(2,4-dimethylphenyl)-1,3,5-triazine are suspended in 100 ml of toluene, and 100 ml of 1N NaOH and 1 g of tetrabutylammonium bromide are added. The mixture is heated for 10 minutes at 80° C. and then cooled, to give a yellow paste. 12.3 ml (0.15 mol) of epibromohydrin are added to this paste and the mixture is again heated for 6 hours at 50° C. When the reaction is complete, methylene chloride is added to the organic phase, which is separated off from the aqueous phase and filtered through Hyflo. It is then evaporated and the crystalline residue is recrystallized from toluene. This gives 14 g of pale yellow crystals, 2-(2-hydroxy-4-glycidyloxyphenyl)-4,6-bis(2,4-dimethylphenyl)-1,3,5-triazine (Compound 44), melting point 152°–155° C.

Example 7

9.07 g (0.02 mol) of Compound 44 and 7.95 g (0.02 mol) of 2-(2,4-dihydroxyphenyl)-4,6-bis(2,4-dimethylphenyl)-1,3,5-triazine are suspended in 150 ml of xylene. 0.2 g of dimethylaminopyridine are added and the mixture is heated at reflux temperature. The reaction is complete after 4 hours. The mixture is diluted with 200 ml of toluene and cooled. In the course of this the product is precipitated. It is filtered off and purified further by recrystallization from toluene together with a little Fuller's earth. This gives 9.1 g of pale beige crystals, 1,3-bis-{4-[4,6-di-(2,4-dimethylphenyl)-s-triazine-2-yl]-3-hydroxy-phenoxy}-2-hydroxypropane (Compound 45), melting point: 222°–224° C.

Example 8

18.5 g (0.05 mol) of 2-(2,4-dihydroxyphenyl)-4,6-bis-(4-methylphenyl)-1,3,5-triazine (Helv. Chim. Acta 55, 1566 (1972)) and 3.9 g (0.05 mol) of potassium methoxide are suspended in 200 ml of anhydrous n-butanol, and 7.4 g (0.06 mol) of butyl chloroacetate are added dropwise between 50° C. and 100° C. After 17 hours under reflux the solvent is evaporated and the crude product is washed with water, dried and recrystallized from petroleum ether (boiling point 110° C.–140° C.) (Compound No. 46).

Melting point: 142°–146° C. Calcd. C 72.03 H 6.04N 8.69% Found C 71.88 H 6.01N 8.81%

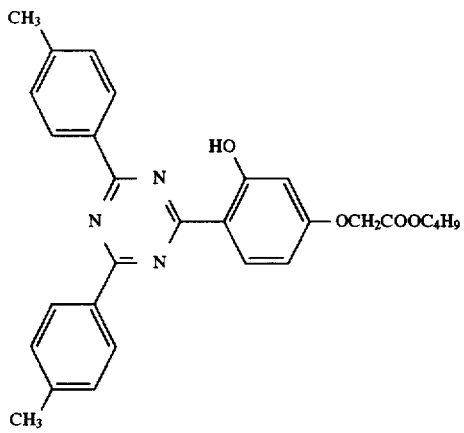

46

Example 9

A) 55.4 g (0.15 mol) of 2-(2,4-dihydroxyphenyl)-4,6-bis-(4-methylphenyl)-1,3,5-triazine are dissolved in refluxing 2-butanone (11) in the presence of 27.6 g (0.2 mol) of $K_2CO_3$. A catalytic amount (0.2 g) of KI is added, and 36.8 g (0.3 mol) of ethyl chloroacetate are added dropwise over 1 h30. After refluxing for 25 h, the reaction mixture is cooled in ice, the precipitate is filtered off, washed with water to neutrality and then with methanol. Drying in the oven yields the analytically pure 2-(2-hydroxy-4-ethoxycarbonylmethoxyphenyl)-4,6-bis-(4-methylphenyl)-1,3,5-triazine (54 g, m.p. 166°–167° C.) (Compound No. 47).

B) 11.4 g (0.025 mol) of compound 47 and 3.9 g (0.03 mol) of octanol (isomeric mixture) are refluxed in 120 ml xylene for 22 h in the presence of 0.62 g (2.5 mmol) of dibutyltinoxide. During the reaction a xylene/ethanol mixture is distilled off, the xylene being replenished dropwise from a dropping funnel. The reaction mixture is cooled to 40° C., filtered through a pad of Prolith and evaporated. Drying at 100° C./0.01 mmHg affords the transesterification product as a viscous yellow oil (12.5 g) that solidifies to a wax (Compound No. 48).

Calcd. C=73.44%, H=6.91%, N=7.79% Found C=72.95%, H=6.70%, N=7.48%

Compounds No. 49 to 52 (Table 4) are obtained analogously by transesterification with the corresponding alcohols.

TABLE 4

| Compound | n | $R_8$ | Physical data |
|---|---|---|---|
| 49 | 1 | $-CH_2CH_2OCH_3$ | m.p. 150–153° C. |
| 50 | 2 | $-CH_2CH_2OCH_2CH_2OC_2H_5$ | m.p. 118–121° C. |
| 51 | 1 | $-(CH_2)_6-$ | m.p. 235–238° C. |
| 52 | 4 | $+CH_2)_4C$ | m.p. 219–231° C. |

Example 10

40.6 g (0.11 mol) of 2-(2,4-dihydroxyphenyl)-4,6-bis-(4-methylphenyl)-1,3,5-triazine are dissolved in refluxing 2-butanone (500 ml) in the presence of 20.7 g (0.15 mol) of $K_2CO_3$. 18.1 g (0.055 mol) of 1,12-dibromodecane dissolved in 100 ml of 2-butanone are added dropwise over 3 h and the mixture is refluxed for 35 h. In the course of this, precipitation of the final product occurs. The reaction mixture is cooled in ice, the precipitate is filtered off, washed with water to neutrality and then with methanol. Drying in the oven affords 46.2 g of the analytically pure compound No. 53 (Table 5). Off-white solid, m.p. 219°–220° C.

Analogous treatment with 1,6-dibromohexane or epibromohydrin gives compounds No. 54 and 55 (Table 5).

TABLE 5

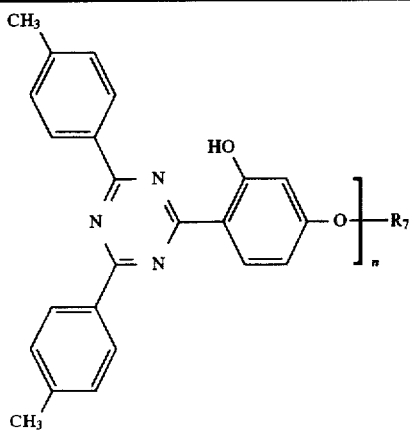

| Compound | n | R$_7$ | Physical data |
|---|---|---|---|
| 53 | 2 | —(CH$_2$)$_{12}$— | m.p. 219–220° C. |
| 54 | 2 | —(CH$_2$)$_6$— | m.p. 247–249° C. |
| 55 | 1 | —CH$_2$—CH(—O—)CH$_2$ (epoxide) | m.p. 205–208° C. |
| 56 | 1 | —CH$_2$—CH(OH)—CH$_2$—OC$_4$H$_9$ | m.p. 166–167° C. |
| 57 | 1 | —CH$_2$—CH(OH)—CH$_2$—O—CH$_2$—CH(C$_2$H$_5$)—C$_4$H$_9$ | m.p. 123–125° C. |
| 58 | 1 | —CH$_2$—CH(—)—CH$_2$—O—CH—[CH$_2$—OCH$_2$—CH(—O—)—CH$_2$]$_2$ (with C(CH$_3$)$_2$ bridge) | Yellow oil<br>calc. / found<br>C 66.02% / 64.52%<br>H 6.89% / 6.98%<br>N 5.63% / 5.23% |
| 59 | 1 | —CH$_2$—CH(OH)—CH$_2$—O—C(=O)—C(CH$_3$)=CH$_2$ | m.p. 183–185° C. |
| 60 | 1 | —CH$_2$—CH(OH)—CH$_2$—O—C(=O)—C$_9$H$_{18}$ | m.p. 135–138° C. |
| 61 | 2 | —OC—(CH$_2$)$_8$—CO— | m.p. 220–228° C. |

Example 11

A mixture of 14.8 g (0.04 mol) of 2-(2,4-dihydroxyphenyl)-4,6-bis-(4-methylphenyl)-1,3,5-triazine, 10.4 g (0.08 mol) of butylglycidylether and 2.1 g (6.5 mmol) of tetratabutylammoniumbromide is refluxed in 150 ml of 2-butanone during 85 h. The reaction mixture is cooled in ice, the precipitate is filtered off, washed with water and methanol, and dried in the oven. This yields 17.5 g of a pale yellow solid, m.p. 166°–167° C. (Compound No. 56, Table 4).

Analogous treatment with the corresponding glycidyl ethers or esters yields the compounds 57 to 60 (Table 4).

Example 12

A solution of 3.6 g (0.015 mol) of sebacyl chloride in 10 ml toluene is added dropwise at 10° C. to a solution of 2-(2,4-dihydroxyphenyl)-4,6-bis(4-methylphenyl)-1,3,5-triazine and 3.3 g (0.033 mol) of triethylamine in 100 ml toluene and 50 ml of DMF. After 50 h at room temperature, the reaction mixture is diluted with water, filtered, the precipitate is washed with water, methanol and chloroform, and dried in the oven. 8.7 g of the diester 61 (Table 4) are obtained as a pale beige solid, m.p. 220°–228° C.

Example 13

When 20.5 g (0.06 mol) of 2-(2,4-dihydroxyphenyl)-4,6-diphenyl-1,3,5-triazine are treated with 22.8 g (0.12 mol) of 2-ethylhexyl glycidyl ether analogously to example 11, 23.3 g of the pale yellow compound No. 62 (m.p. 116° to 118° C.) are obtained.

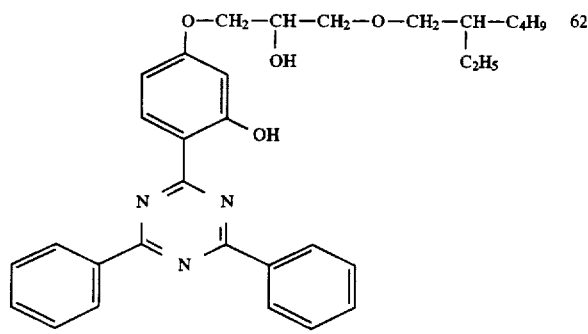

62

Example 14

7.9 g (0.02 mol) of 2-(2,4-dihydroxyphenyl)-4,6-bis(2,4-dimethylphenyl)-1,3,5-triazine, 5.7 g (0.02 mol) of a technical mixture of dodecyl, tridecyl and tetradecyl glycidyl ethers (Araldite® DY 025) and 0.15 g of ethyl triphenylphosphonium iodide in 50 ml of mesitylene are heated at 160°–165° C. for 10 hours, with stirring. The reaction solution is washed with water, dried over MgSO₄, and filtered. The filtrate is stirred for 2 hours with 2 g of Filtrol 4, filtered and evaporated in vacuo. The residue is freed from residual mesitylene at 120° C. and 0.01 mmHg. This leaves 12.1 g of an oil (Compound No. 63).

$C_{41}H_{55}N_3O_4$ Calcd. C75.30 H8.48 N6.43% Found. C75.0 H8.1N 6.8%

APPLICATION EXAMPLES

Example 15
Stabilization of a 2-Coat Metallic Coating

A clear lacquer is prepared by mixing the following components:

| | |
|---|---|
| 59.2 | Parts of a commercial acrylic resin (Uracron ® XB 2263, DMS Resins BV, NL) which is a 50% solution in xylene, |
| 11.6 | parts of a 90% melamine resin (Cymel ® 327, Amer. Cyanamid Corp.) |
| 19.4 | parts of xylene |
| 5.5 | parts of butylgylcol acetate |
| 9.3 | parts of butanol |
| 1.0 | part of a levelling agent (Baysilon ® A, Bayer AG) which is a 1% solution in xylene |
| 100 | parts lacquer containing 40% solids. |

Samples of this lacquer are mixed with 0.5% (related to the solids) of di(1,2,2,6,6-pentamethylpiperidin-4-yl) sebacate (=HA-1) and 1.5% (related to the solids) of a triazine stabilizer listed in table 6.

The clear lacquer is diluted to a sprayable state with a mixture of 13:6:1 xylene/butanol/butyl glycol acetate and is sprayed onto a previously prepared aluminum sheet (coil-coated and primed with a silver-metallic paint based on polyester/cellulose acetobutyrate/melamine resin), and the sheet is baked for 30 minutes at 130° C. This results in a dry film thickness of 40–50 µm of clear lacquer. A clear lacquer containing no light stabilizer is used as a comparison.

The samples are exposed in a UVCON. Type UVB-313, weathering equipment with a cycle of 8 hrs of dry UV irradiation at 70° C. and 4 hrs of condensation at 50° C. The 20°-gloss of the samples is measured in certain intervals of weathering time using the method of DIN 67530. The results are given in Table 6.

TABLE 6

| Piperidin Stabilizer | Triazine Stabilizer (Compound No.) | 20°-Gloss after exposure of | | | | |
|---|---|---|---|---|---|---|
| | | 0 | 1600 | 3200 | 4800 | 6400 hrs |
| — | — | 86 | 31 | — | — | — |
| 0.5% HA-1 | 1.5% 1 | 86 | 79 | 74 | 77 | 61 |
| 0.5% HA-1 | 1.5% 30 | 86 | 74 | 68 | 66 | 57 |
| 0.5% HA-1 | 1.5% 32 | 82 | 69 | 72 | 68 | 59 |
| 0.5% HA-1 | 1.5% 33 | 85 | 79 | 74 | 72 | 64 |

Example 16

The preparation of the samples and their testing is the same as in Example 15. As comparison C-1 and C-2, two triazine derivatives known from U.S. Pat. No. 4,619,956, are used as triazine stabilizers.

C-1=2-(2-hydroxy-4-dodecyloxyphenyl)-4,6-diphenyl-1,3,5-triazine

C-2=2-(2-hydroxy-4-octadecyloxyphenyl)-4,6-diphenyl-1,3,5-triazine

The results are shown in Table 7.

TABLE 7

| Piperidin Stabilizer | Triazine Stabilizer | 20°-Gloss after exposure of | | | |
|---|---|---|---|---|---|
| | | 0 | 1600 | 3200 | 4000 hrs |
| — | — | 84 | 19 | — | — |
| 0.5% HA-1 | 1.5% Compound 34 | 84 | 80 | 78 | 59 |
| 0.5% HA-1 | 1.5% Compound 35 | 85 | 81 | 80 | 75 |
| 0.5% HA-1 | 1.5% Compound 36 | 85 | 80 | 78 | 76 |
| 0.5% HA-1 | 1.5% Compound 37 | 85 | 80 | 79 | 77 |
| 0.5% HA-1 | 1.5% Compound 39 | 85 | 81 | 72 | 74 |
| 0.5% HA-1 | 1.5% C-1 | 85 | 54 | 35 | 37 |
| 0.5% HA-1 | 1.5% C-2 | 79 | 38 | 34 | 37 |

Example 17

A similar clear lacquer is prepared from

| | |
|---|---|
| 54.5 | parts of Uracron ® XB 2263 |
| 16.3 | parts of Cymel ® 327 |
| 19.4 | parts of xylene |
| 5.5 | parts of butylgylcol acetate |
| 3.3 | parts of butanol |
| 1 | part of Baysilon ® A |
| 100 | parts lacquer containing 41.5% solids. |

Samples of this lacquer are mixed with 0.5% (related to the solids) of HA-1 and 1.5% (related to the solids) of a triazine stabilizer listed in Table 8. The lacquer is diluted to a sprayable state by diluting with a 13:6:1 mixture of xylene/butanol/butylglycol acetate and is sprayed onto an aluminium sheet which is coil coated and primed with a metallic blue commercial paint (Glasomax®, Glasurit GmbH, Münster). Mter baking for 30 minutes at 130° C. the clear lacquer layer has a thickness of 40–45 µm.

The samples are weathered in a UVCON, Type UVB 313, as described in Example 15 and the 20°-gloss of the weathered samples is measured according to method DIN 67530. The results are shown in Table 8.

TABLE 8

| Piperidin Stabilizer | Triazine Stabilizer (Compound No.) | 20°-Gloss after exposure of | | | |
|---|---|---|---|---|---|
| | | 0 | 800 | 1600 | 2000 hrs |
| — | — | 85 | 75 | 42 | 20— |
| 0.5% HA-1 | 1.5%   4 | 86 | 80 | 78 | 78 |
| 0.5% HA-1 | 1.5%   6 | 87 | 81 | 81 | 81 |
| 0.5% HA-1 | 1.5%   7 | 85 | 81 | 81 | 79 |
| 0.5% HA-1 | 1.5%  10 | 86 | 82 | 80 | 80 |
| 0.5% HA-1 | 1.5%  11 | 86 | 81 | 81 | 78 |
| 0.5% HA-1 | 1.5%  17 | 86 | 81 | 81 | 81 |
| 0.5% HA-1 | 1.5%  18 | 87 | 81 | 80 | 80 |
| 0.5% HA-1 | 1.5%  62 | 84 | 80 | 78 | 81 |

Example 18

The two-coat samples are prepared as described in Example 15, however, no piperidin stabilizer is added. The samples are weathered in a Weatherometer with cycle CAM 159 and with using an edge filter of type A. Measured is the 20°-gloss before and after exposure, the results are shown in Table 9.

TABLE 9

| Triazine Stabilizer (Compound No.) | 20°-Gloss after exposure of | | |
|---|---|---|---|
| | 0 | 2000 | 3600 hrs |
| none | 85 | 47 | 25 |
| 34 | 86 | 71 | 64 |
| 35 | 86 | 72 | 61 |
| 36 | 86 | 73 | 60 |

Example 19

The two-coat samples are prepared as described in Example 17, however, no piperidin stabilizer is added. The samples are weathered in a UVCON, type UVB-313 with cycle of 8 hrs of UV irradiation at 70° C. and 4 hrs of condensation at 50° C. The 20°-gloss of the sample is measured according to method DIN 67530 before and after exposure. Further the change of colour shade $\Delta E$ after exposure is measured according to method DIN 6174. The results are shown in Table 10.

TABLE 10

| Triazine Stabilizer (Compound No.) | 20°-Gloss after exposure of | | | $\Delta E$ |
|---|---|---|---|---|
| | 0 | 800 | 1600 hrs | after 1600 h |
| none | 85 | 75 | 42 | 6.6 |
| 6 | 84 | 80 | 80 | 1.3 |
| 7 | 84 | 81 | 80 | 1.3 |
| 17 | 86 | 81 | 80 | 1.6 |
| 18 | 86 | 81 | 80 | 1.4 |
| 62 | 86 | 82 | 81 | 1.0 |

Example 20

Stabilization of a radiation-curable system A clear lacquer is prepared by mixing 14 parts of tris(2-acryloyloxyethyl) isocyanurate with 6 parts of 1,6-hexanediol diacrylate and 0.4 parts of 1-benzoylcyclohexanol (as photoinitiator). A triazine stabilizer is added in an amount of 1.5%. The lacquer is coated to a white coil-coated aluminium sheet in a dry-thickness of about 40 μm.

The samples are hardened by UV irradiation in a PPG processor (2×80 W/cm, 2×10 m (min)) and weathered in a UVCON, type UVB-313 with a cycle of 4 hours of UV irradiation at 60° C. and 4 hrs of condensation at 50° C.

The yellowness index (method ASTM D 1925-70) of the samples is measured before and after the exposure. The results are shown in Table 11.

TABLE 11

| Triazine Stabilizer (Compound No.) | Yellowness Index after exposure of | | | |
|---|---|---|---|---|
| | 0 | 200 | 400 | 600 hrs |
| none | −1.0 | 19.6 | 28.0 | 35.3 |
| 1.5%  17 | −0.6 | 1.8 | 1.8 | 2.1 |

What is claimed is:

1. A composition comprising:

(a) an organic material selected from the group consisting of organic polymers, fats, waxes, oils, cosmetics, and photographic material, which organic material is stabilized against damage caused by light, heat, and oxygen by the presence of (b) at least one sterically hindered amine of the polyalkylpiperidine type, and (c) at least one o-hydroxyphenyl-s-triazine of the formula:

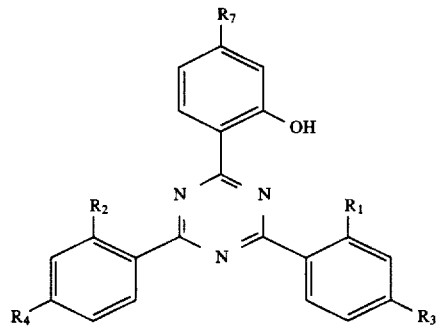

wherein:
R1 is alkyl of 1 to 12 carbon atoms;
R2 is alkyl of 1 to 12 carbon atoms;
R3 is alkyl of 1 to 12 carbon atoms;
R4 is alkyl of 1 to 12 carbon atoms; and
R7 is:
  (i) alkoxy of 1 to 12 carbon atoms substituted with hydroxy; or
  (ii) alkoxy of 1 to 12 carbon atoms which is substituted with alkoxy of 1–18 carbon atoms and hydroxy.

2. A composition according to claim 1 wherein each of $R_1$, $R_2$, $R_3$, and $R_4$ is methyl and $R_7$ is —OCH$_2$CH(OH)CH$_2$OR in which R is an alkyl of 1 to 18 carbon atoms.

3. A composition according to claim 2 wherein R is butyl.

4. A composition according to claim 2 wherein R is octyl.

5. A composition according to claim 2 wherein R is alkyl of 12–14 carbon atoms.

6. A composition according to claim 1 wherein in said o-hydroxyphenyl-s-triazine, each of $R_1$, $R_2$, $R_3$, and $R_4$ is methyl.

7. A composition according to claim 1, wherein said sterically hindered amine containing at least one group of the formula:

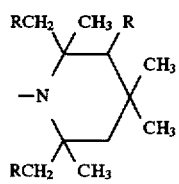

in which R is hydrogen or methyl.

8. A composition according to claim 7, wherein R is hydrogen.

9. A composition according to claim 7, wherein said sterically hindered amine is (i) di-(2,2,6,6-tetramethylpiperidin-4-yl) succinate; (ii) di-(2,2,6,6-tetramethylpiperidin-4-yl) sebacate; (iii) di-(1,2,2,6,6-pentamethylpiperidin-4-yl)sebacate; (iv) di-(1,2, 2,6,6-pentamethylpiperidin-4-yl) butyl-(3,5-di-tert-butyl-4-hydroxybenzyl)-malonate; (v) di-(1-octyloxy-2,2,6,6-tetramethylpiperidin-4-yl) sebacate; (vi) tetra-(2,2, 6,6-tetramethylpiperidin-4-yl) butane-1,2,3,4-tetracarboxylate; (vii) tetra-(1,2,2,6,6-pentamethylpiperidin-4-yl) butane-1,2, 3,4-tetracarboxylate; (viii) N-(2,2,6,6-tetramethylpiperidin-4-yl)-β-aminopropionic acid dodecyl ester; (ix) N-(1-octyloxy-2,2,6,6-tetramethylpiperidin-4-yl)-N'-dodecyl-oxalamide; (x) N-(2,2,6,6-tetramethylpiperidin-4-yl)-α-dodecylsuccinimide; (xi) 2,2,4,4-tetramethyl-7-oxa-3,20-diaza-21-oxo-dispiro|5.1.11.2|heneicosane; (xii) 8-acetyl-3-dodecyl-1,3,8-triaza-7,7,9,9-tetramethylspirol|4.5|decane-2,4-dione; (xiii) 20-(dodecyloxycarbonylethyl)-2,2,4,4-tetramethyl-7-oxa-3,20-diaza-221-oxo-dispiro-|5.1.11.2| heneicosane; (xiv) a compound of the formula:

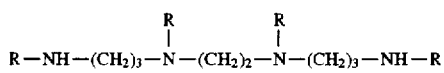

in which R is

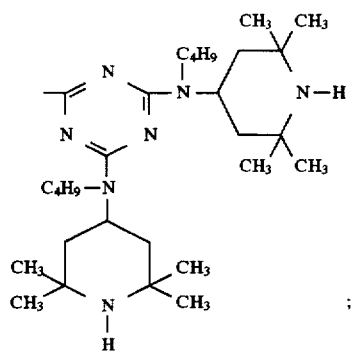

(xv) a compound of the formula:

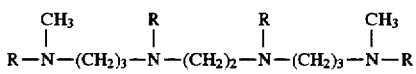

in which R is

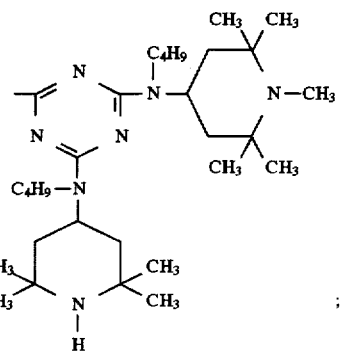

(xvi) a compound of the formula:

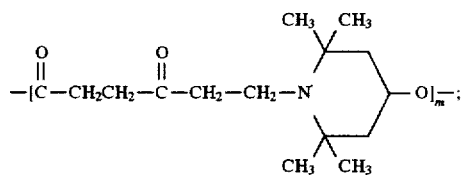

(xvii) a compound of the formula:

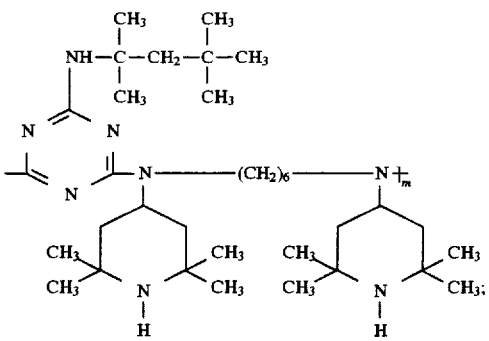

(xviii) a compound of the formula:

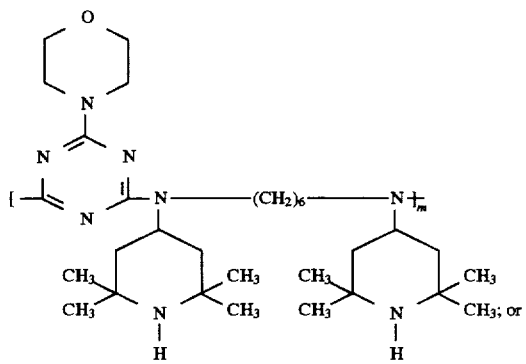

(xix) a compound of the formula:

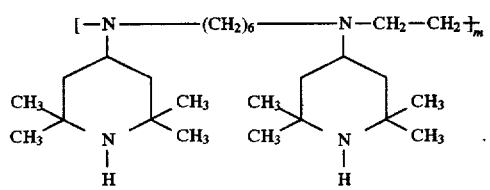

in which m has a value of from 2 to about 200.

10. A composition according to claim 1 which contains 0.01 to 5% by weight of said sterically hindered amine and 0.02 to 5% by weight of said o-hydroxyphenyl-s-triazine, relative to said organic material.

11. A composition according to claim 10 which contains 0.02 to 2% by weight of said sterically hindered amine and 0.05 to 3% by weight of said o-hydroxyphenyl-s-triazine.

12. A composition according to claim 1 wherein the organic material is an organic polymer.

13. A composition according to claim 12, which, in addition to said sterically hindered amine and said o-hydroxyphenyl-s-triazine also contains further stabilizers, fillers, reinforcing agents, pigments, dyes, plasticizers, solvents, lubricants, flow-control agents, fluorescent brighteners, nucleating agents, antistatic agents or fire-retarding agents.

14. A composition according to claim 12, wherein the polymer is a coating binder.

15. A composition according to claim 1, wherein the material is a radiation-curable coating material.

16. A process for stabilizing an organic material selected from the group consisting of organic polymers, fats, waxes, oils, cosmetics and photographic materials against damage caused by exposure to light, heat and oxygen, which comprises incorporating into said organic material an effective stabilizing amount of at least one sterically hindered amine of the polyalkylpiperidine type and at least one o-hydroxyphenyl-s-triazine of the formula:

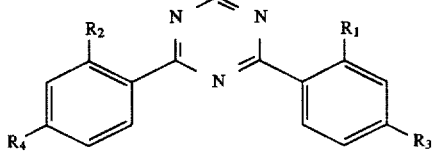

wherein:

$R_1$ is alkyl of 1 to 12 carbon atoms;

$R_2$ is alkyl of 1 to 12 carbon atoms;

$R_3$ is alkyl of 1 to 12 carbon atoms;

$R_4$ is alkyl of 1 to 12 carbon atoms; and $R_7$ is:
  (i) alkoxy of 1 to 12 carbon atoms substituted with hydroxy; or
  (ii) alkoxy of 1 to 12 carbon atoms which is substituted with alkoxy of 1–18 carbon atoms and hydroxy.

17. The process of claim 16, wherein said organic material is an organic polymer.

18. The process of claim 17, wherein said organic polymer is a polycarbonate.

19. The process of claim 17, wherein said organic polymer is a radiation-curable coating material.

* * * * *